(12) United States Patent
Wei

(10) Patent No.: US 8,517,985 B2
(45) Date of Patent: Aug. 27, 2013

(54) NEEDLE INSERTION ASSISTANCE DEVICE

(76) Inventor: Deye Wei, Brooklyn, NY (US)

( * ) Notice: Subject to any disclaimer, the term of this patent is extended or adjusted under 35 U.S.C. 154(b) by 707 days.

(21) Appl. No.: 12/025,830

(22) Filed: Feb. 5, 2008

(65) Prior Publication Data

US 2008/0154198 A1   Jun. 26, 2008

(51) Int. Cl.
*A61M 5/00* (2006.01)

(52) U.S. Cl.
USPC ........... 604/117; 604/171; 604/172; 604/173; 604/174; 604/176; 604/177; 604/178; 604/179; 604/180; 604/181; 604/165.04

(58) Field of Classification Search
USPC .................. 604/171–181, 165.04, 165.05
See application file for complete search history.

(56) References Cited

U.S. PATENT DOCUMENTS

| | | | |
|---|---|---|---|
| 780,147 A | 1/1905 | Wilcox et al. ................ 604/224 |
| 2,047,010 A | 7/1936 | Dickinson ..................... 604/157 |
| 2,198,666 A | 4/1940 | Gruskin ........................ 604/117 |
| 2,316,095 A | 4/1943 | Mead, Jr. ...................... 604/209 |
| 2,451,183 A * | 10/1948 | Tantimonaco ................ 604/115 |
| 2,531,267 A | 11/1950 | Harnisch ....................... 604/126 |
| 3,819,091 A | 6/1974 | Hollender ..................... 222/327 |
| 4,067,334 A | 1/1978 | Haller ............................ 128/218 |
| 4,198,975 A | 4/1980 | Haller ............................ 128/218 |
| 4,231,368 A | 11/1980 | Becker .......................... 128/218 |
| 4,403,987 A * | 9/1983 | Gottinger ...................... 604/115 |
| 4,465,478 A | 8/1984 | Sabelman et al. ............ 604/224 |
| 4,594,073 A | 6/1986 | Stine ............................. 604/187 |
| 4,838,857 A * | 6/1989 | Strowe et al. .................. 604/67 |
| 4,897,080 A | 1/1990 | Hamidi ......................... 604/117 |
| 5,047,036 A * | 9/1991 | Koutrouvelis ................ 606/130 |
| 5,115,816 A | 5/1992 | Lee ............................... 128/749 |
| 5,241,969 A | 9/1993 | Carson et al. ................ 128/753 |
| 5,280,427 A * | 1/1994 | Magnusson et al. .......... 600/407 |
| 5,400,666 A | 3/1995 | Song ........................... 73/864.21 |
| 5,469,860 A * | 11/1995 | De Santis ..................... 600/578 |
| 5,607,581 A * | 3/1997 | Gerner et al. .............. 210/198.2 |
| 5,665,095 A * | 9/1997 | Jacobson ...................... 606/130 |
| 5,830,152 A * | 11/1998 | Tao ............................... 600/562 |
| 6,047,861 A * | 4/2000 | Vidal et al. .................... 222/137 |
| 6,283,425 B1 * | 9/2001 | Liljevik ...................... 248/230.4 |
| 6,607,512 B2 * | 8/2003 | Oliver et al. .................. 604/209 |
| 7,497,863 B2 * | 3/2009 | Solar et al. ................... 606/130 |
| 2001/0047151 A1 * | 11/2001 | Xian et al. .................... 604/117 |

* cited by examiner

*Primary Examiner* — Nicholas Lucchesi
*Assistant Examiner* — Scott Medway
(74) *Attorney, Agent, or Firm* — Walter J. Tencza, Jr.

(57) ABSTRACT

A needle insertion assistance device is provided to easily hold a needle device, which comprises a syringe and a needle having a needle wing and being attached to the syringe, in order to more reliably control the advancement of the needle during insertion of the needle into a targeted part of a human body for many medical purposes. One embodiment of the needle insertion assistance device may comprise a supporting plate, a base connected hingedly to a rear surface of the supporting plate, and a syringe holder securely affixed to a top surface of the base to slidably hold the syringe on the base and prevent the syringe from moving from side to side. This embodiment of the needle insertion assistance device may further include a needle blocker, a handle, and an angle adjusting assembly.

13 Claims, 12 Drawing Sheets

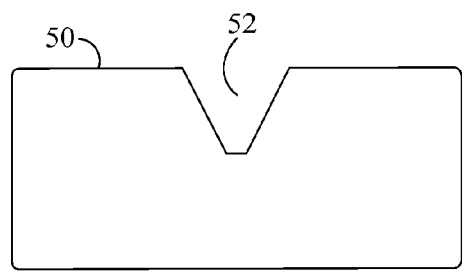
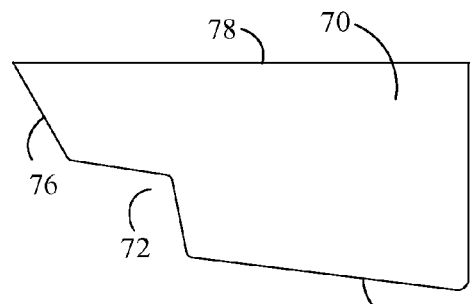
FIG. 17　　　　　　　FIG. 18
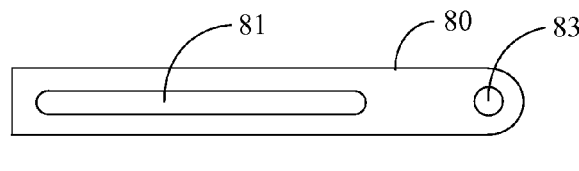
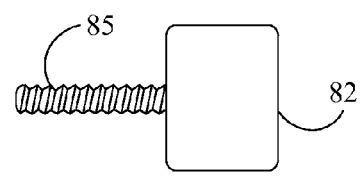
FIG. 19　　　　　　　FIG. 20
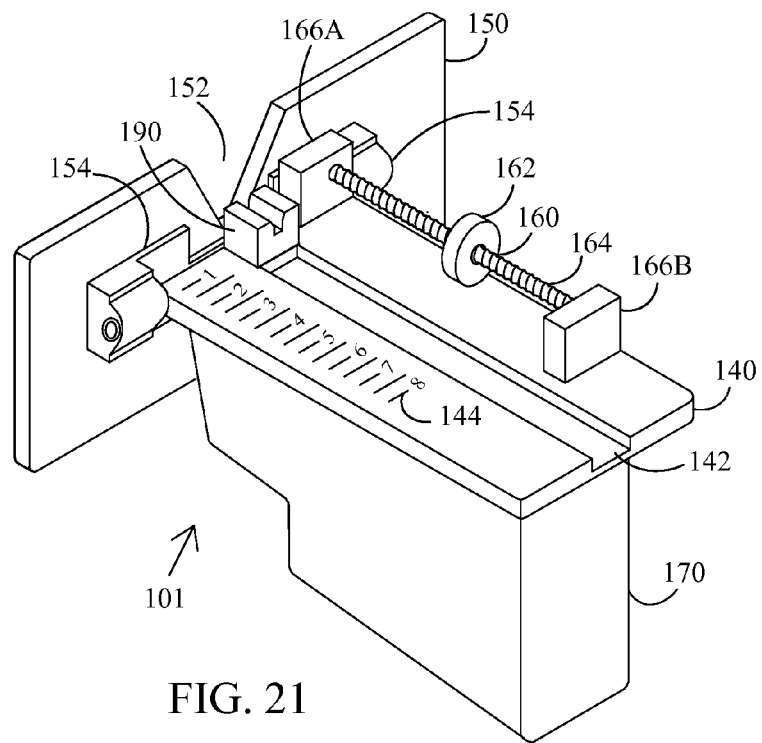
FIG. 21

NEEDLE INSERTION ASSISTANCE DEVICE

FIELD OF THE INVENTION

This invention relates to improved methods and devices concerning use of needles and syringes.

BACKGROUND OF THE INVENTION

A needle may need to be inserted into a part of a human body for many medical purposes. For example, needles are used for placing a catheter, for administrating drugs into certain parts of a human body, or for drawing blood or fluid from blood vessels or cavities. For an epidural anesthesia, a needle needs to be inserted into a narrow epidural space to place a catheter. To be inserted into the epidural space, the needle is typically held directly by one or two human hands, and then inserted into a human patient's back. After the needle is inserted into the interspinous ligament through the skin of the human patient, it is usually advanced about one millimeter in each attempt of advancement. Each attempt of advancement is followed by a loss of resistance technique to identify if the needle enters the epidural space. After the needle is inserted into the epidural space, a catheter is inserted through the needle into the epidural space followed by removal of the needle. A drug can be given through the catheter, which remains in the epidural space during epidural anesthesia.

It is not easy to hold the needle directly with a person's hands, such as with a physician's hands. Since the epidural space is very narrow, the needle can be unintentionally advanced through the epidural space into the subarachnoid space, even into the spinal cord, due to sudden movement of the patient or too much advancement of the needle. The side effect of headache may develop if the needle is inserted through the epidural space into the subarachnoid space. It is critical to hold the needle and control the advancement of the needle to avoid advancing the needle through the epidural space into the subarachnoid space or the spinal cord.

To draw blood or fluid from a human's blood vessels or cavities, a needle is held directly by one or two hands of a person, such as a physician. It is not easy to hold the needle directly and control advancement of the needle, especially when the patient is not cooperative.

A depth controller for an epidural needle, referred to in U.S. published patent application no. 20010047151 A1, incorporated by reference herein, discloses a device for holding a syringe and an epidural needle with a needle wing, and controlling the advancement of the epidural needle insertion. That device includes a screw that can block the advancement of the epidural needle to prevent over-advancement. However, it is easy to advance the epidural needle together with the device itself forward and unintentionally over-advance the epidural needle. It is not easy to hold that device, since there is no handle.

SUMMARY OF THE INVENTION

At least one embodiment of the present invention provides a device, which may be called a needle insertion assistance device, to easily hold a needle device, which comprises a syringe and a needle with a needle wing, and to more reliably control the advancement of the needle during insertion of the needle into a targeted part of a human body for placing a catheter, administrating a drug, or drawing blood or fluid. The targeted part of the human body may be an epidural space, blood vessels, and cavities of the human body.

One embodiment of the present invention includes a supporting plate, a base hingedly connected to a rear surface of the supporting plate, and a syringe holder securely affixed to a top surface of the base. This embodiment further includes a needle blocker securely affixed to one side of the top surface of the base, a handle securely affixed to an underside of the base, and an angle adjusting assembly having two ends and being pivotally connected to the rear surface of the supporting plate at one end and slidably connected to the base at another end.

The base may further include a groove longitudinally furrowed on the top surface of the base to hold a syringe and act as a track for the syringe to advance in a straight line. The needle blocker may still further include a screw bolt, a screw nut screwed on the screw bolt, and at least one screw support. The angle adjusting assembly may still further include an arm, an arm screw, and an arm support.

A needle, which has a needle wing, may be attached to a syringe to form a needle device. The needle device may be then placed on the needle insertion assistance device with the syringe placed in the groove and the syringe holder, and the needle wing on the top surface of the base. The supporting plate supports the needle insertion assistance device on the human body, and prevents unintentional forward advancement of the needle insertion assistance device together with the needle device to prevent unintentional over-advancement of the needle. The needle blocker may block the advancement of the needle of the needle device by blocking the needle wing to advance forward beyond the location of the screw nut to prevent unintentional over-advancement of the needle. The handle increases the whole size of the needle insertion assistance device and facilitates handling and hand-held usage of the needle insertion assistance device. The angle adjusting assembly stops rotation of the base with respect to the supporting plate to fix an angle of the base with respect to the supporting plate to stabilize an angle at which the needle is inserted into the human body.

BRIEF DESCRIPTION OF THE DRAWINGS

FIG. 17 is a rear plan view of a supporting plate for use with the needle insertion assistance device of FIG. 1;

FIG. 18 is a lateral plan view of a handle for use with the needle insertion assistance device of FIG. 1;

FIG. 19 is a lateral plan view of an arm of an angle adjusting assembly for use with the needle insertion assistance device of FIG. 1;

FIG. 20 is a lateral plan view of an arm screw of the angle adjusting assembly for use with the needle insertion assistance device of FIG. 1;

FIG. 21 is a rear, top, left side perspective view of a needle insertion assistance device in accordance with a second embodiment of the present invention;

DETAILED DESCRIPTION OF THE DRAWINGS

Figure 1:
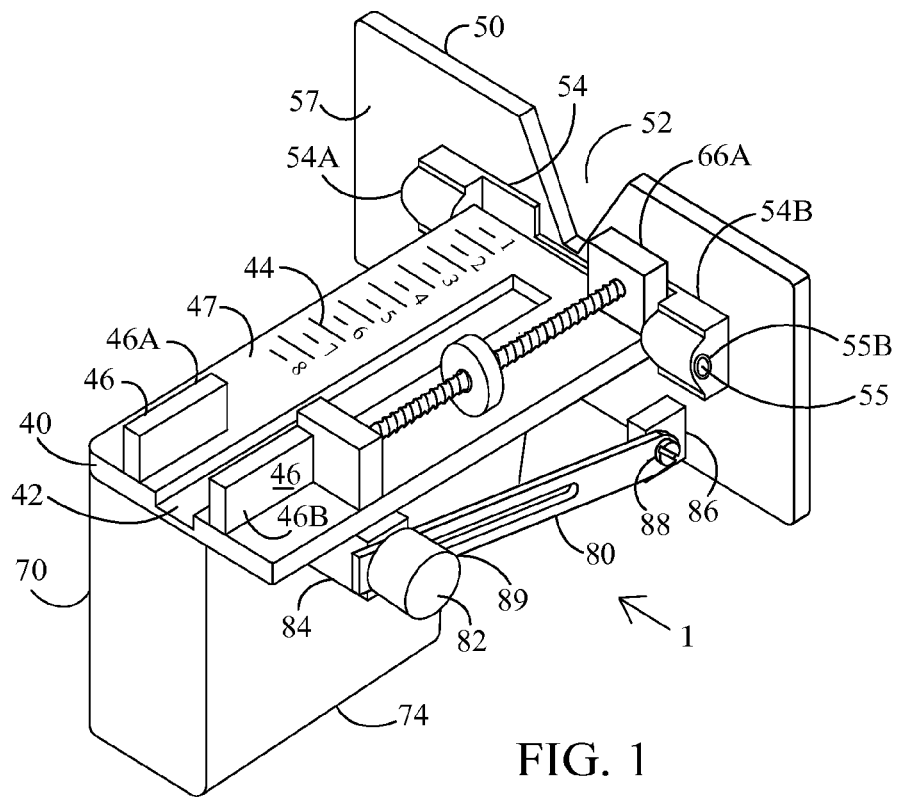
FIG. 1 is a rear, top, and right side perspective view of a first embodiment of a needle insertion assistance device.
Figure 2:
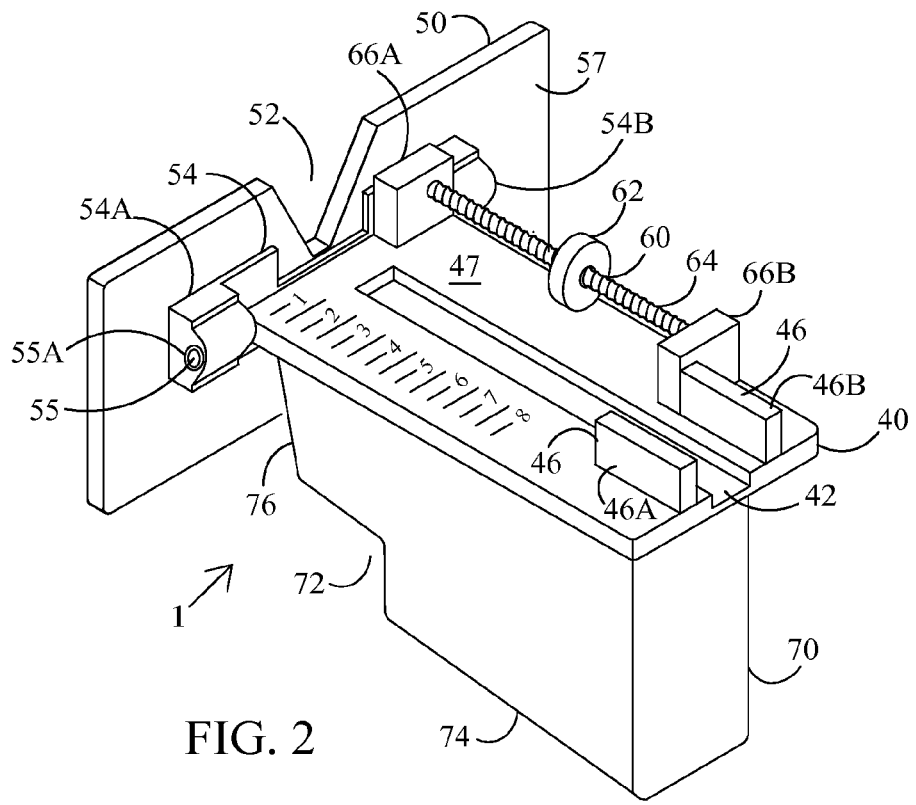
FIG. 2 is a rear, top, and left side perspective view of the needle insertion assistance device of FIG. 1.
Figure 3:
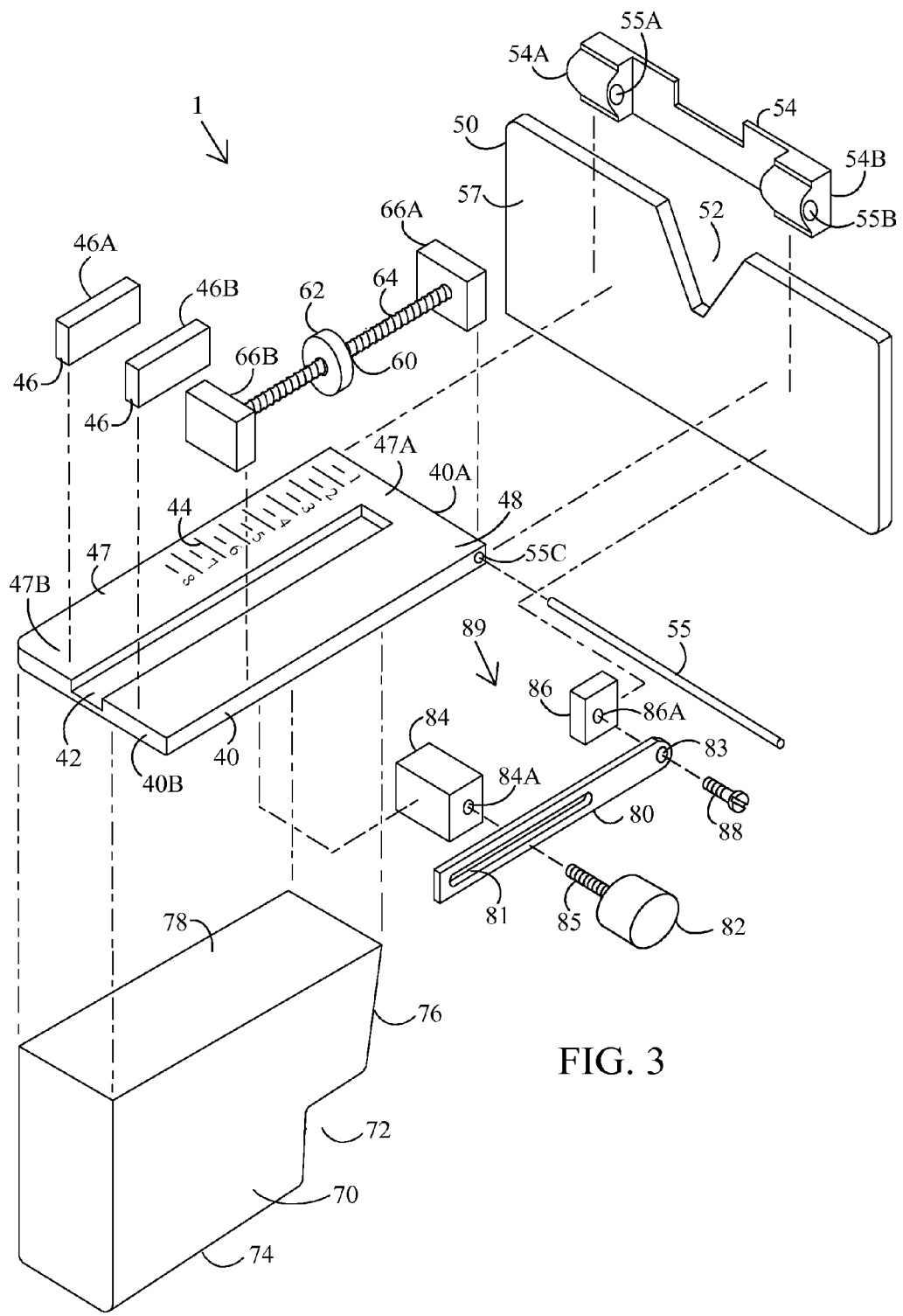
FIG. 3 is an exploded, rear, top, and right side perspective view of the needle insertion assistance device of FIG. 1.

FIG. 1 is a rear, top, right side perspective view of a needle insertion assistance device 1 in accordance with a first embodiment of the present invention. FIG. 2 is a rear, top, left side perspective view of the needle insertion assistance device 1 of FIG. 1. FIG. 3 is an exploded, rear, top, right side perspective view of the needle insertion assistance device 1 of FIG. 1.

As shown in FIGS. 1, 2, and 3, the needle insertion assistance device 1 of FIG. 1 includes a base 40, a supporting plate 50, and a syringe holder 46. The base 40 is connected to the supporting plate 50 by a joint, pivot, or hinge 54. The needle insertion assistance device 1 of FIG. 1 further includes a needle blocker 60, a handle 70, and an angle adjusting assembly 89.

As shown in FIG. 3, the base 40 further includes a groove 42, a hinge hole 55C, an underside, a top surface 47, a front end 40A, a rear end 40B, and a set of ruler marks 44 marked on the top surface 47. The top surface 47 still further includes a front part 47A, a rear part 47B, and two sides, such as a side 48. The syringe holder 46 further includes a left syringe holding plate 46A, and a right syringe holding plate 46B. The left syringe holding plate 46A and the right syringe holding plate 46B may be a means for holding the syringe 106 of the needle device 107 on the base 40. The supporting plate 50 further includes a front surface, a rear surface 57, and a needle gap 52. The needle blocker 60 further includes a screw bolt 64 having two ends, a screw nut 62 screwed on the screw bolt 64, a front screw support 66A, and a rear screw support 66B. The handle 70 further includes a notch 72, a bottom 74, a front 76, and a top 78 as shown in FIGS. 3 and 18. The hinge 54 further includes a left side 54A with a hinge hole 55A, a right side 54B with a hinge hole 55B, and a hinge pin 55 as shown in FIG. 3. The hinge 54 and the hinge pin 55 may be a means for connecting the front end 40A of the base 40 to the rear surface 57 of the supporting plate 50.

As shown in FIGS. 1, 2 and 3, the front end 40A of the base 40 is connected to the rear surface 57 of the supporting plate 50 by the hinge 54, with the hinge pin 55 inserted through the hinge holes 55B, 55C, and 55A, and the hinge 54 securely affixed to the rear surface 57 of the supporting plate 50. The left syringe holding plate 46A and the right syringe holding plate 46B of the syringe holder 46 are securely affixed to the rear part 47B of the top surface 47 of the base 40, on both sides of the groove 42 respectively. The front screw support 66A and the rear screw support 66B are securely affixed to each end of the screw bolt 64 respectively, and securely affixed to one side, such as the side 48, of the top surface 47 of the base 40 to support the screw bolt 64 and the screw nut 62 over the side of the top surface 47 of the base 40. The top 78 of the handle 70 is securely affixed to the underside of the base 40.

As shown in FIG. 3, the angle adjusting assembly 89 further includes an arm 80, an arm screw 82, and an arm support 84. The arm 80 has two ends, and has a sliding gap 81 in one end, and a pivot hole 83 in another end, as shown in FIGS. 3, and 19. The arm screw 82 further includes an arm screw bolt 85 as shown in FIGS. 3 and 20. The arm support 84 further includes a support screw hole 84A as shown in FIG. 3. At one end, the arm 80 is pivotally connected to the rear surface 57 of the supporting plate 50 by an arm hinge, arm joint, or arm pivot 86. At another end, the arm 80 is slidably connected to the arm support 84 by the arm screw 82 with the arm screw bolt 85 inserted through the sliding gap 81 of the arm 80 and screwed into the support screw hole 84A of the arm support 84. The arm support 84 is securely affixed to the underside of the base 40, so that the arm 80 can slide with respect to the arm support 84 and the base 40 over the arm screw bolt 85 of the arm screw 82 when the arm screw 82 is turned and screwed into a loose state. The arm pivot 86 is securely affixed to the rear surface 57 of the supporting plate 50. The arm pivot 86 further includes a pivot screw hole 86A, and a pivot screw 88 as shown in FIG. 3. The pivot screw 88 is inserted through the pivot hole 83 of the arm 80 and then screwed into the pivot screw hole 86A to pivotally connect the arm 80 to the rear surface 57 of the supporting plate 50.

In one embodiment of the present invention, the front end 40A of the base 40 is connected to the rear surface 57 of the supporting plate 50 by the hinge 54, as shown in FIGS. 1 and 2. However, in alternative embodiments, the front end 40A of the base 40 may be securely affixed to the rear surface 57 of the supporting plate 50 at various degree angles from about ninety to one hundred and sixty degrees between the top surface 47 of the base 40 and the rear surface 57 of the supporting plate 50 above the connection site.

Figure 4:
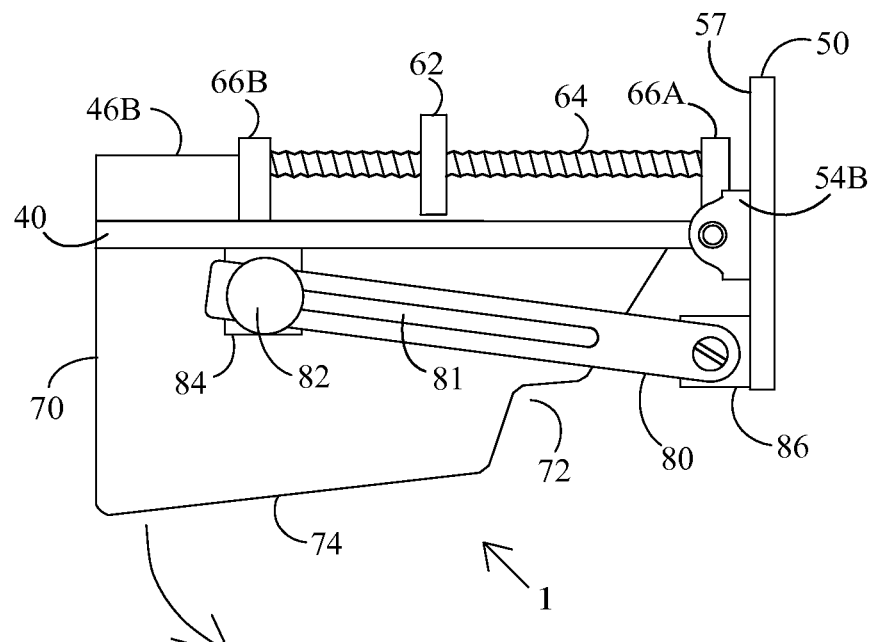
FIG. 4 is a lateral right side plan view of the needle insertion assistance device of FIG. 1, with the needle insertion assistance device of FIG. 1 in a first state.
Figure 5:
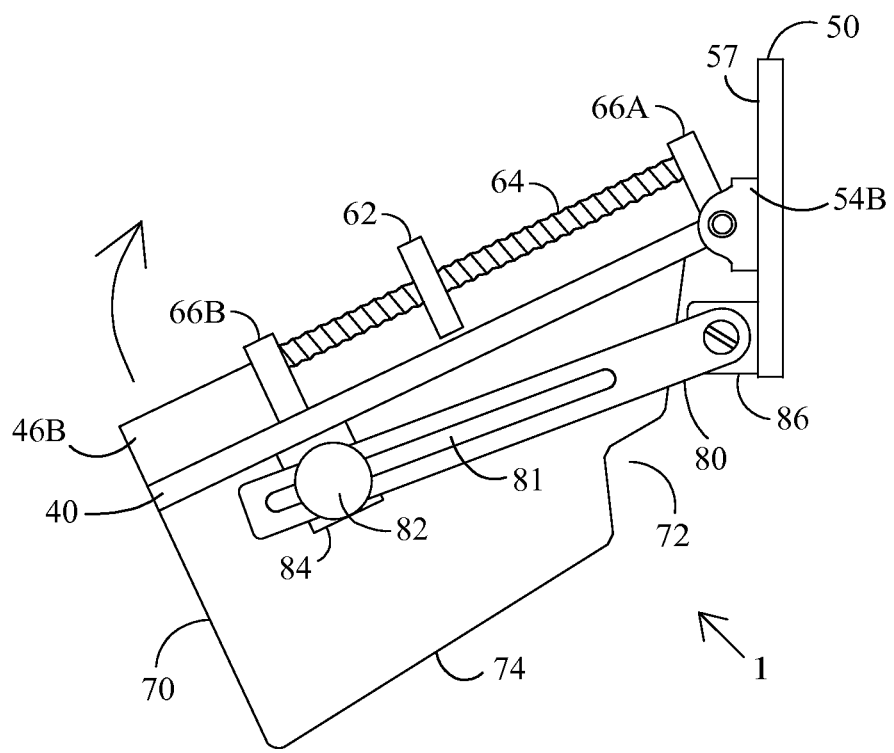
FIG. 5 is a lateral right side plan view of the needle insertion assistance device of FIG. 1, with the needle insertion assistance device of FIG. 1 in a second state.
Figure 6:
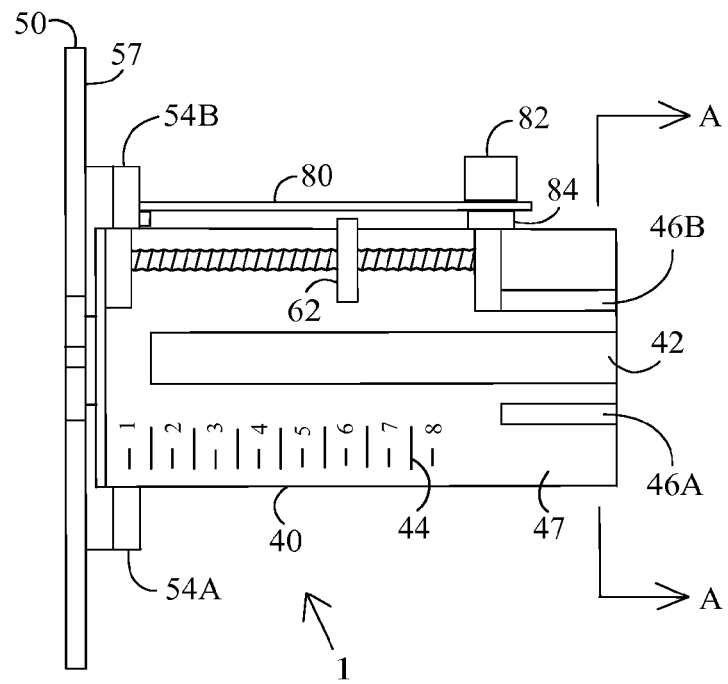
FIG. 6 is a top plan view of the needle insertion assistance device of FIG. 1.

FIG. 4 is a lateral right side plan view of the needle insertion assistance device 1 of FIG. 1, with the needle insertion assistance device 1 of FIG. 1 in a first state. In the first state, the base 40 is substantially perpendicular to the supporting plate 50. FIG. 5 is a lateral right side plan view of the needle insertion assistance device 1 of FIG. 1 in a second state. In the second state, the base 40 has been rotated downward on the hinge 54 to form a different angle with the supporting plate 50, so that the base 40 is no longer perpendicular to the supporting plate 50. FIG. 6 is a top plan view of the needle insertion assistance device 1 of FIG. 1.

Figure 7:
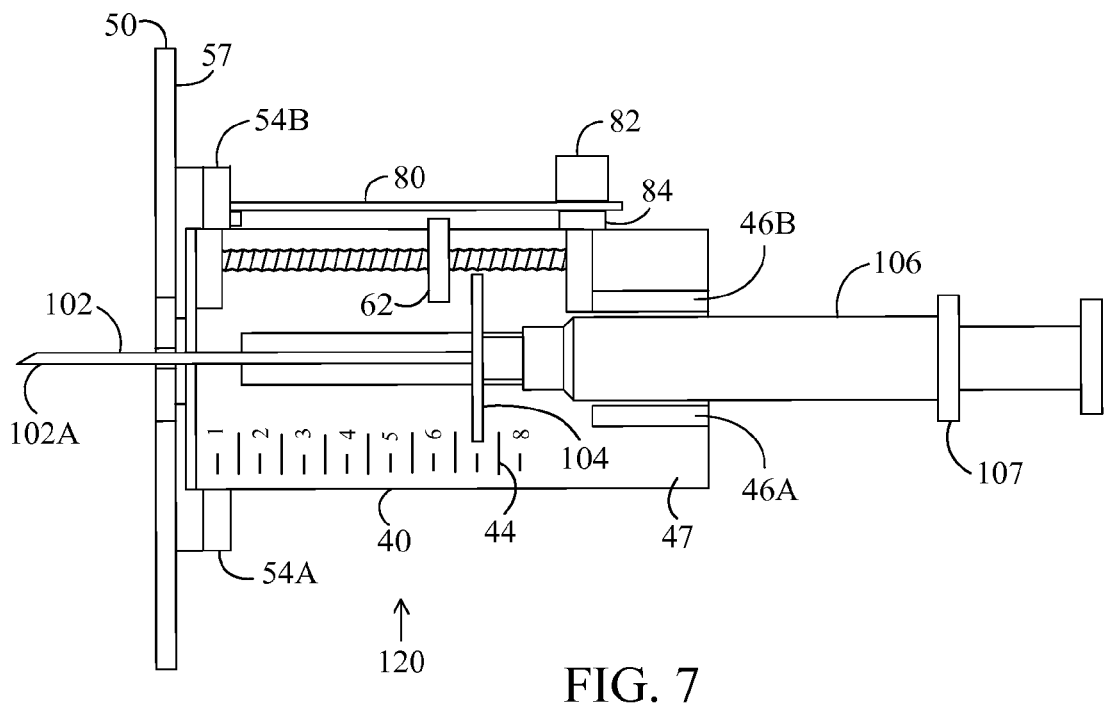
FIG. 7 is a top plan view of the needle insertion assistance device of FIG. 1 along with a needle device comprising a syringe and a needle having a needle wing, illustrating how the needle insertion assistance device of FIG. 1 holds the needle device.
Figure 8:
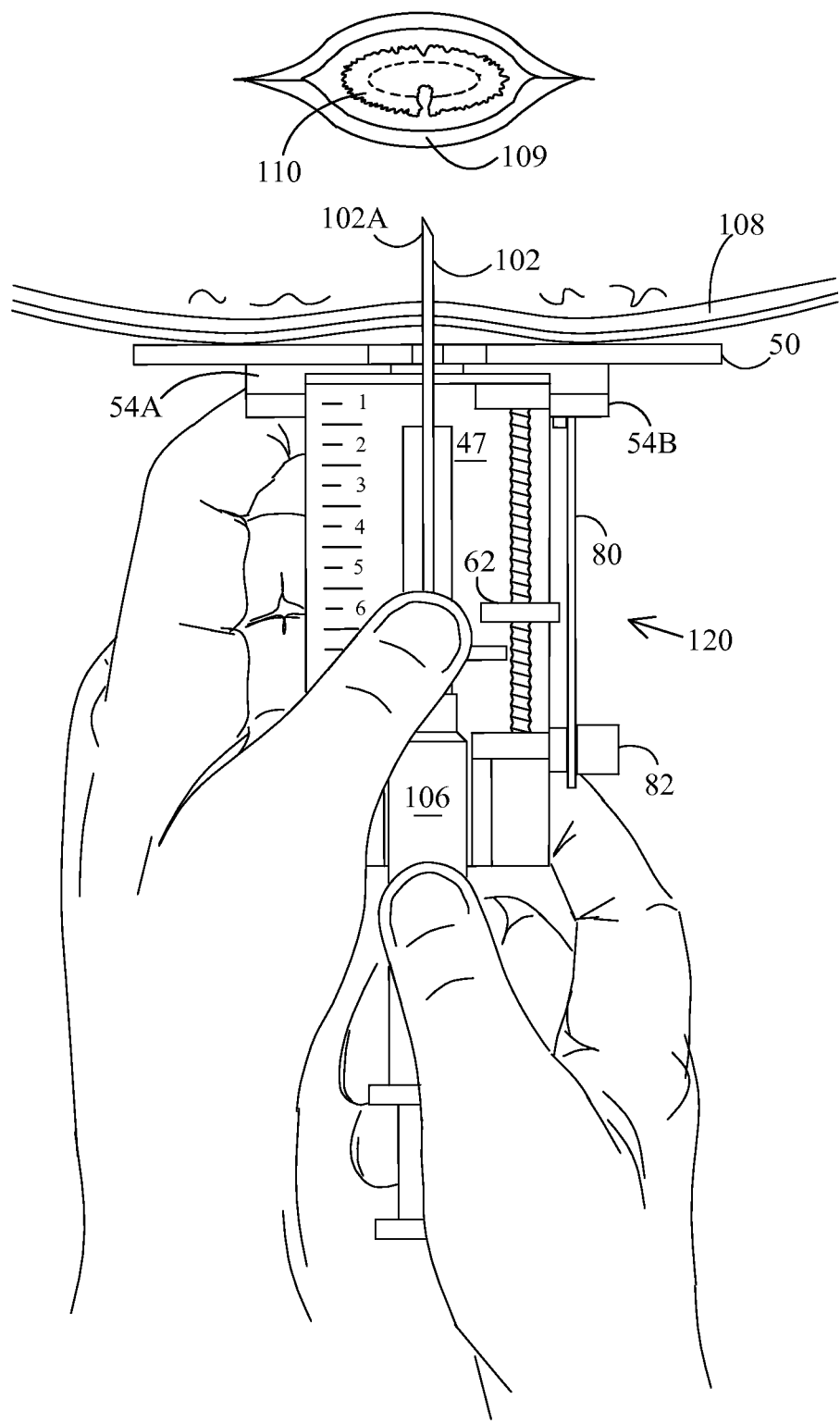
FIG. 8 is a partial cross-section view of a skin, a spinal cord, and an epidural space of a human body, and a top plan view of the needle insertion assistance device of FIG. 1 along with the needle device, illustrating how a user holds the needle insertion assistance device of FIG. 1 along with the needle device.
Figure 9:
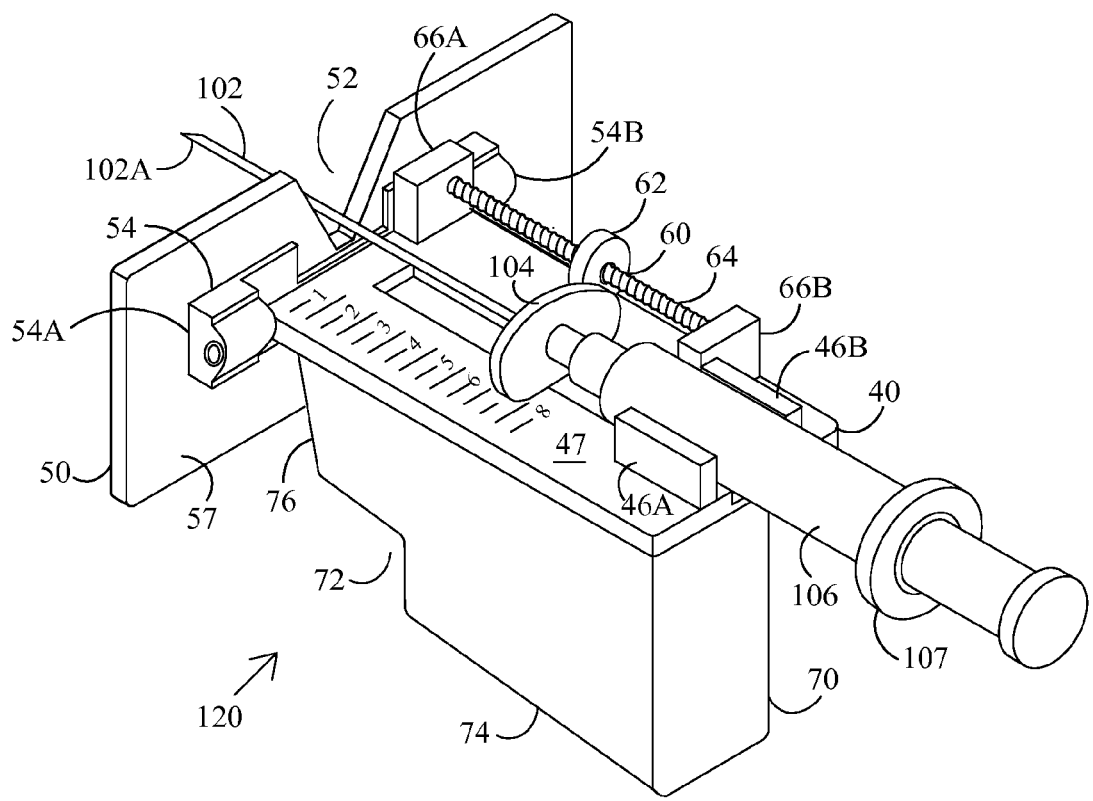
FIG. 9 is a rear, top, left side perspective view of the needle insertion assistance device of FIG. 1 along with the needle device.

FIG. 7 is a top plan view of the needle insertion assistance device 1 of FIG. 1 along with a needle device 107 placed into the needle insertion assistance device 1 of FIG. 1 to form an apparatus 120 of FIG. 7. The needle device 107 further comprises a syringe 106, and a needle 102 that has a needle wing 104 and is attached to the syringe 106. FIG. 8 is a partial cross-section view through a skin 108, a spinal cord 110 and an epidural space 109 of a human body, and a top plan view of the apparatus 120 of FIG. 7, illustrating how a user holds the apparatus 120 of FIG. 7, which comprises the needle insertion assistance device 1 of FIG. 1 and the needle device 107 placed into the needle insertion assistance device 1 of FIG. 1. FIG. 9 is a rear, top, left side perspective view of the apparatus 120 of FIG. 7.

The needle device 107 is currently used in practice in the United States, such as a needle device comprising a glass syringe and a Tuohy needle, with the Tuohy needle being attached to the glass syringe. The Tuohy needle has a needle wing affixed to the hub of the Tuohy needle. The glass syringe and the Tuohy needle with the needle wing are available from Becton, Dickinson and Company, New Jersey, the United States of America.

As shown in FIGS. 3, 8 and 17, the supporting plate 50 may be a support, or plate to support the apparatus 120 of FIG. 7 on a surface of a human body, such as the skin 108, where the needle 102 is inserted. The supporting plate 50 acts as to prevent a user of the apparatus 120 of FIG. 7 from advancing the apparatus 120 of FIG. 7 forward together with the needle device 107 to avoid unintentional over-advancement of the needle 102, because the supporting plate 50 significantly increases the area where the apparatus 120 of FIG. 7 has direct contact with the human body, and increases the resistance to the forward advancement of the apparatus 120 of FIG. 7.

In one embodiment of the present invention, the supporting plate 50 has a rectangle shape in a front and a rear plan views, with exception of the needle gap 52, as shown in FIGS. 3, and 17. However, the supporting plate 50 may have a different shape, such as a polygon, a circle, an ellipse, and/or a combination of a polygon, a circle, and an ellipse, etc. The needle gap 52 may be a slot, notch, or gap cut at an upper part of the supporting plate 50 for the needle 102 to pass through the supporting plate 50. The needle gap 52 has a substantially triangular shape as shown in FIGS. 3, and 17. However, the needle gap 52 may have a different shape, such as a polygon, a semicircle, a semi-ellipse, and/or a combination of a polygon, a semicircle, and a semi-ellipse, etc. In alternative embodiments, the needle gap 52 may be modified to form an opening or hole cut through the supporting plate 50 that allow the needle 102 to pass through the supporting plate 50 to perform the same function as the needle gap 52.

Figure 10:
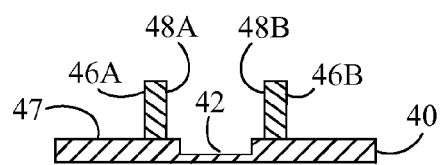
FIG. 10 is a cross-section view of a base and a syringe holder for use with the needle insertion assistance device of FIG. 1, along a line A-A shown in FIG. 6.
Figure 11:
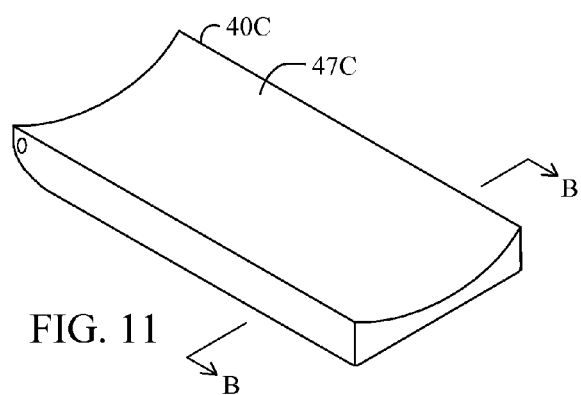
FIG. 11 is a rear, top, left side perspective view of another embodiment of a base as an alternative for the base shown in FIG. 10, for use with the needle insertion assistance device of FIG. 1, excluding the base shown in FIG. 1.
Figure 12:
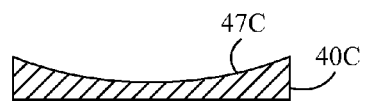
FIG. 12 is a cross-sectional view of the base of FIG. 11, along a line B-B shown in FIG. 11.

As shown in FIGS. 1-3, 9 and 10, the base 40 may be a support, plate, or base to support the screw supports 66A and 66B, the syringe holder 46, the needle wing 104 of the needle 102, and the syringe 106. The top surface 47 of the base 40 is approximately flat to support the needle wing 104 of the needle 102, and to allow the needle wing 104 of the needle 102 to smoothly slide and advance forward as shown in FIGS. 9 and 10. In one embodiment of the present invention, the top surface 47 of the base 40 is an approximately flat surface, as shown in FIGS. 3 and 10. However, the top surface 47 may be different, such as a curved top surface, an angular surface, and/or a combination of a flat surface, an angular surface, and a curved surface, etc. to accommodate the configuration of the bottom of the needle wing 104 of the needle 102 so that the needle wing 104, as well as the needle device 107, is able to advance forward smoothly. FIGS. 11 and 12 show a curved surface 47C of a base 40C as an example of some alternative embodiments of the top surface 47 of the base 40.

In one embodiment of the present invention, the base 40 may have a longitudinal length about the same as the length of the syringe 106, a width about three to four times of the diameter of the syringe 106, and a thickness from about half one millimeter to five millimeters. However, the base 40 may have different sizes, with different longitudinal lengths, widths, and thicknesses in alternative embodiments.

The groove 42 shown in FIGS. 1-3, may be an indentation, recess, or groove longitudinally furrowed in the top surface 47 of the base 40, between the left syringe holding plate 46A and the right syringe holding plate 46B of the syringe holder 46, and from the edge of the rear end 40B of the base 40 toward the edge of the front end 40A of the base 40. In one embodiment of the present invention, the distance between the edge of the front end of the groove 42 and the edge of the front end 40A of the base 40 may be less than about six centimeters. However, the distance between the edge of the front end of the groove 42 and the edge of the front end 40A of the base 40 may be more than about six centimeters. In some alternative embodiments of the present invention, the groove 42 may be a groove longitudinally furrowed from the edge of the rear end 40B of the base 40 throughout to the edge of the front end 40A of the base 40 on the top surface 47 of the base 40. The longitudinal length of the groove 42 may be from about half of the longitudinal length of the base 40 to the longitudinal length of the base 40. In one embodiment of the present invention, the depth of the groove 42 may be at least about one millimeter. However, the depth of the groove 42 may be from about half one millimeter to the full thickness of the base 40. The width of the groove 42 may be smaller than the diameter of the syringe 106 so that the groove 42 can receive a part of one side of the syringe 106, whereby the groove 42 acts as a recess to hold the syringe 106 on the base 40 and as a track for the syringe 106 to advance in a straight line.

Figure 14:
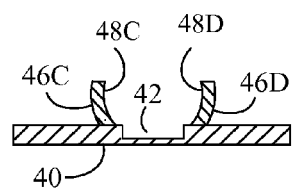
FIG. 14 is a cross-section view of the base and the syringe holder of FIG. 13, along a line C-C shown in FIG. 13.

In one embodiment, the groove 42 has a rectangular cross section, as shown in FIGS. 3, 10 and 14. However, the groove 42 may have a different cross section, or may be replaced by a groove with a different cross section, such as a partial semicircular cross section, as shown for a groove 42A in FIGS. 15 and 16, a partial semi-elliptical cross section, a triangular cross section, a polyangular cross section, and/or a combination of a partial semicircular cross section, a partial semi-elliptical cross section, a triangular cross section, a polyangular cross section, etc.

In one embodiment of the present invention, as shown in FIGS. 1-3, the groove 42 may be longitudinally furrowed in about a middle part of the top surface 47 of the base 40. However, the groove 42 may be longitudinally furrowed in different part of the top surface 47 of the base 40, such as in about a left side part, or a right side part of the top surface 47 of the base 40.

As shown in FIGS. 3, 6 and 7, the base 40 further includes at least one set of ruler marks 44 marked on the top surface 47 of the base 40 to indicate how far the needle 102 of the needle device 107 advances with each attempt of the advancement. In one embodiment, the set of ruler marks 44 is marked with a centimeter unit system. In alternative embodiments, the set of ruler marks 44 may be marked with a different unit system, such as a millimeter unit system, or an inch unit system, etc.

The hinge 54, as shown in FIGS. 1, 2 and 3, may be a mechanism that connects the front end 40A of the base 40 to the rear surface 57 of the supporting plate 50 so that the base 40 may be turned around on the hinge 54 to form different angles with respect to the supporting plate 50, according to an angle at which the needle 102 is inserted into a human body. In one embodiment of the present invention, the base 40 is connected to the supporting plate 50 by the hinge 54 or other hinges. In alternative embodiments, the base 40 may be connected to the supporting plate 50 by other mechanisms, such as a pivot, or a joint, etc., so that the base 40 may be turned around to form different angles with respect to the supporting plate 50.

In one embodiment of the present invention, as shown in FIGS. 1, 2 and 3, the front end 40A of the base 40 is connected to about a middle part of the rear surface 57 of the supporting plate 50 by the hinge 54. However, in some alternative embodiments, the front end 40A of the base 40 may be connected to a different part of the rear surface 57 of the supporting plate 50 by the hinge 54, such as, to about a left side part, a right side part, a lower part, or an upper part of the rear surface 57 of the supporting plate 50, to function satisfactorily.

Figure 13:
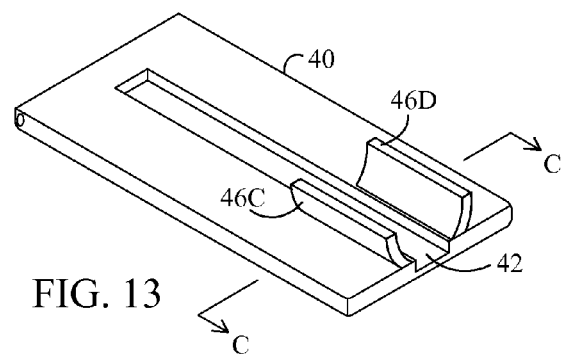
FIG. 13 is a rear, top, left side perspective view of the base of FIGS. 6 and 10 for use with the needle insertion assistance device of FIG. 1, excluding the syringe holder shown in FIG. 1, along with an alternative embodiment of a syringe holder.

The left syringe holding plate 46A and the right syringe holding plate 46B of the syringe holder 46, as shown in FIGS. 2, 6, and 10, may be two protrusions, projections, or plates securely affixed to the rear part 47B of the top surface 47 of the base 40, on both sides of the groove 42 respectively. The left syringe holding plate 46A has an internal surface 48A, and the right syringe holding plate 46B has an internal surface 48B. The syringe holder 46 holds the syringe 106 on the groove 42 of the base 40, and allow the syringe 106 to slide within a space formed by the left syringe holding plate 46A and the right syringe holding plate 46B of the syringe holder 46, and prevents the syringe 106 from moving from side to side. The distance between the left syringe holding plate 46A and the right syringe holding plate 46B may be slightly longer than the diameter of the syringe 106 so that the left syringe holding plate 46A and the right syringe holding plate 46B may slidably hold the syringe 106 on the groove 42 to allow the syringe 106 to be able to smoothly slide forward in a straight line and, but to be unable to move moving from side to side, as shown in FIGS. 7 and 9. In some embodiments of the present invention, the longitudinal length of the left syringe holding plate 46A and the right syringe holding plate 46B may be about half one centimeter to seven centimeters so that the left syringe holding plate 46A and the right syringe holding plate 46B may keep the syringe 106 substantially in a straight line on the groove 42 while the syringe 106 slides within the space between the left syringe holding plate 46A and the right syringe holding plate 46B. However, the longitudinal length of the left syringe holding plate 46A and the right syringe holding plate 46B may be longer than seven centimeters or less than a half centimeter to function satisfactorily. In one embodiment of the present invention, the left syringe holding plate 46A and the right syringe holding plate 46B have approximately the same longitudinal length. However, the left syringe holding plate 46A and the right syringe holding plate 46B may have a different longitudinal length. In one embodiment of the present invention, the internal surface 48A of the left syringe holding plate 46A and the internal surface 48B of the right syringe holding plate 46B, that have direct contact with the syringe 106, may be substantially flat surfaces as shown in FIG. 10. However the internal surfaces 48A and 48B may be different, such as curved surfaces, angular surfaces, and/or combinations of flat surfaces, curved surfaces, and angular surfaces, etc., to accommodate the configuration of the both sides of the syringe 106 to hold the syringe 106 so that the syringe 106 is able to advance forward smoothly, but unable to move from side to side. FIGS. 13 and 14 show a curved internal surface 48C of a syringe holding plate 46C and a curved internal surface 48D of a syringe holding plate 46D as an example of some alternative embodiments of the internal surfaces 48A and 48B.

Figure 15:
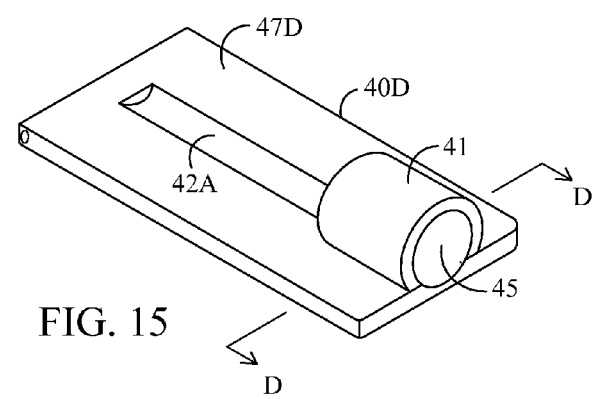
FIG. 15 is a rear, top, left side perspective view of an alternative embodiment of a base and a syringe holder for use with the needle insertion assistance device of FIG. 1, excluding the base and the syringe holder shown in FIG. 1.
Figure 16:
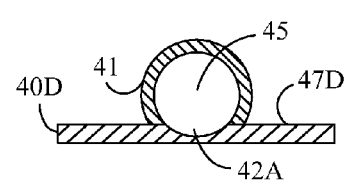
FIG. 16 is a cross-section view of the base and the syringe holder of FIG. 15, along a line D-D shown in FIG. 15.

FIGS. 15 and 16 show one embodiment of a syringe holder 41, and a base 40D having a top surface 47D and a groove 42A for use with the needle insertion assistance device 1 of FIG. 1, excluding the base 40 and the syringe holder 46. The syringe holder 41 is a hollow cylinder having a syringe holding opening, syringe holding tunnel, or syringe holding hole 45 cut through the syringe holder 41. The diameter of the syringe holding hole 45 may be slightly larger than the diameter of the syringe 106 to allow the syringe holding hole 45 to hold the syringe 106 fairly tightly, but allow the syringe 106 to slide smoothly within the syringe holding hole 45. As shown in FIGS. 15 and 16, the syringe holder 41 is securely affixed to the rear part of the top surface 47D of the base 40D, opposite to the front end of the base 40D that is connected to the supporting plate 50. The top surface 47D and the base 40D in FIGS. 15 and 16 have the same structure as the top surface 47 and the base 40 in FIGS. 3 and 10, respectively. The syringe holding hole 45 can be combined and used with the groove 42A as shown in the FIGS. 15 and 16. In one embodiment of the present invention, the cross section of the syringe holding hole 45 is substantially circular, as shown in FIG. 16. However the cross section of the syringe holding hole 45 can be different, such as substantially oval, triangular, square, and/or polyangular, etc., to hold the syringe 106 on the base 40D.

In one embodiment of the present invention, the base 40 dose not have a groove, such as the groove 42. In the embodiment without the groove 42, the syringe holder 46 alone can reliably and satisfactorily hold the syringe 106 of the needle device 107 on the base 40 in a straight line, so that the syringe 106, as well as the needle device 107, is able to advance forward in a straight line, but unable to move from side to side.

As shown in FIGS. 1-5, the handle 70 may be a projection, or extension from the underside of the base 40 to increase the whole size of the needle insertion assistance device 1 of FIG. 1 to facilitate handling and hand-held usage of the needle insertion assistance device 1 of FIG. 1 by a human being. The top 78 of the handle 70 is securely affixed to the underside of the base 40. As shown in FIG. 18, the notch 72 is cut and situated between the front 76 and the bottom 74 of the handle 70, and shaped and sized according to the shape and size of an index finger or middle finger of a human being to further facilitate handling and hand-held usage of the needle insertion assistance device 1 of FIG. 1 by the human being. The handle 70 is shaped and sized according to the shape and size of a hand of the human being to facilitate handling and hand-held usage of the needle insertion assistance device 1 of FIG. 1 by the human being.

In alternative embodiments, the handle 70 is not included, because the handle 70 is not needed for these alternative embodiments to stand on a patient's back for insertion of an epidural needle into an epidural space for epidural anesthesia when the patient is in prone position. It is easier for these embodiments without the handle 70 to stand up stably with the supporting plate 50 placed on the patient's back when the patient is prone on a table.

The front screw support 66A and the rear screw support 66B may be two protrusions, projections, or supports securely affixed to each end of the screw bolt 64 respectively, and then securely affixed to one side, such as the side 48, of the top surface 47 of the base 40 to support the screw bolt 64 and the screw nut 62 over the side of the top surface 47 of the base 40, so that the screw nut 62 can block the advancement of the needle device 107 by blocking the needle wing 104 to advance forward beyond the location of the screw nut 62. As shown in FIGS. 7-9, the rear screw support 66B can also hold and support one side of the syringe 106 of the needle device 107, and function as the right syringe holding plate 46B of the syringe holder 46 to prevent the syringe 106 from moving to the right side, so that the rear screw support 66B may be considered to be both the rear screw support 66B itself to support the screw bolt 64 and the right syringe holding plate 46B, or a part of the right syringe holding plate 46B to hold and support the right side of the syringe 106. To advance the needle device 107 further, the user drives forward the screw nut 62 by turning the screw nut 62 forward, and then advances forward the needle device 107. In one embodiment of the present invention, the needle insertion assistance device 1 of FIG. 1 includes both the front screw support 66A and the rear screw support 66B to support the screw bolt 64. However, in alternative embodiments, the needle insertion assistance device 1 of FIG. 1 may include only the front screw support 66A, or only the rear screw support 66B, to support the screw bolt 64 satisfactorily in alternative embodiments.

In one embodiment of the present invention, the syringe holder 46 of the needle insertion assistance device 1 of FIG. 1 includes both the left syringe holding plate 46A and the right syringe holding plate 46B. However, the syringe holder 46 may include only one syringe holding plate, such as the left syringe holding plate 46A, and the rear screw support 66B to satisfactorily hold the syringe 106 on the base 40, with the left syringe holding plate 46A holding the left side of the syringe 106, and the rear screw support 66B holding the right side of the syringe 106 as shown in FIGS. 7, 8 and 9. Therefore, the rear screw support 66B may be considered to be both the rear screw support 66B itself to support the screw bolt 64 and the right syringe holding plate 46B, or a part of the right syringe holding plate 46B, to hold and support the right side of the syringe 106.

In one alternative embodiment, the needle blocker 60 is not included, since the needle blocker 60 is not needed for insertion of the needle 102 into some big cavities of a human body, such as a thoracic cavity with fluid accumulation, because it is not necessary to control advancement of the needle 102 as accurately as for insertion of the needle 102 into a small cavity or space, such as the epidural space 109.

The angle adjusting assembly 89 may be a mechanism to stop the rotation of the base 40 on the hinge 54 to fix an angle of the base 40 with respect to the supporting plate 50 to stabilize an angle at which the needle 102 is inserted into a human body. The angle adjusting assembly 89 may be a means for stopping rotation of the base 40 with respect to the supporting plate 50 to fix an angle of the base 40 with respect to the supporting plate 50 to stabilize an angle at which the needle 102 is inserted into a human body. As shown in FIGS. 3 and 19, the arm 80 of the angle adjusting assembly 89 may be a splint, blade, or arm that has two ends, with the pivot hole 83 in one end and the sliding gap 81 in another end. At one end, the arm 80 is pivotally connected to the rear surface 57 of the supporting plate 50 by the arm pivot 86 with the pivot screw 88 inserted through the pivot hole 83 of the arm 80 and screwed into the pivot screw hole 86A of the arm pivot 86, as shown in FIGS. 1 and 3. The arm pivot 86 is securely affixed to the rear surface 57 of the supporting plate 50. At another end, the arm 80 is slidably connected to the base 40 by the arm support 84 and the arm screw 82. The arm support 84 may be a base, or support securely affixed to the underside of the base 40. In alternative embodiments, the arm support 84 may also be securely affixed to a side of the handle 70 or a side of the base 40. The arm screw bolt 85 of the arm screw 82, as shown in FIGS. 3 and 20, is inserted through the sliding gap 81 of the arm 80 and screwed into the support screw hole 84A of the arm support 84, so that the arm 80 is able to slide with respect to the arm support 84 and the base 40 over the arm screw bolt 85 of the arm screw 82. When the arm screw 82 is turned and driven into a tight state, the arm 80 is not able to slide with respect to the arm support 84 and the base 40 over the arm screw bolt 85 of the arm screw 82, and then the base 40 is not able to rotate on the hinge 54 to change the angle of the base 40 with respect to the supporting plate 50, as shown in FIGS. 4 and 5. When the arm screw 82 is turned and driven to a loose state, the arm 80 is then able to slide with respect to the arm support 84 and the base 40 over the arm screw bolt 85 of the arm screw 82, and then the base 40 is able to rotate on the hinge 54 to change the angle of the base 40 with respect to the supporting plate 50, as shown in FIGS. 4 and 5.

In alternative embodiments, the angle adjusting assembly 89 is not included, since the angle adjusting assembly 89 is not needed for an experienced user of the first embodiment of FIG. 1.

In operation, the first embodiment of FIG. 1 functions as follows. To insert the needle 102, which has the needle wing 104, into a targeted tissue or cavity of a human body, the needle insertion assistance device 1 of FIG. 1 can be used as follows. The syringe 106 is attached to the needle 102 to form the needle device 107. The needle device 107 is then placed into the needle insertion assistance device 1 of FIG. 1 to form the apparatus 120 of FIG. 7, as shown in FIGS. 7 and 9, with the needle wing 104 on the top surface 47 of the base 40, and the syringe 106 on the groove 42 and between the left syringe holding plate 46A and the right syringe holding plate 46B, and the needle 102 passing through the needle gap 52 of the supporting plate 50. The screw nut 62 is driven and situated in front of the needle wing 104 as shown in FIGS. 7 and 9.

To use the embodiment of FIGS. 15 and 16 with the syringe holder 41, the syringe 106 is first placed into the syringe holding hole 45, and then attached to the needle 102 with the needle wing 104 to form the needle device 107, with the needle wing 104 on the top surface 47D of the base 40D, the syringe 106 inside the syringe holding hole 45 and the groove 42A, and the needle 102 passing through the needle gap 52 of the supporting plate 50. The screw nut 62 is driven and situated in front of the needle wing 104 similar to that shown in FIGS. 7 and 9.

The base 40 can be rotated on the hinge 54 to form an angle with respect of the supporting plate 50 as the same as an angle at which the needle 102 is going to be inserted into the skin 108. The arm screw 82 is then turned and driven into a tight state to tighten the arm 80 to the arm support 84, so that the arm 80 is unable to slide over the arm screw bolt 85 of the arm screw 82 to allow the angle adjusting assembly 89 to stop the rotation of the base 40 on the hinge 54 to fix the angle of the base 40 with respect to the supporting plate 50 to stabilize the angle at which the needle 102 is going to be inserted into the skin 108. The user's left hand typically holds the apparatus 120 of FIG. 7 with the left thumb over the needle wing 104, the index finger in the space between the front 76 of the handle 70 and the rear surface 57 of the supporting plate 50, and the rest of fingers holding the handle 70 as shown in FIG. 8.

When using the embodiment without the angle adjusting assembly 89, the user's left hand typically holds the apparatus 120 of FIG. 7, excluding the angle adjusting assembly 89, with the left thumb over the needle wing 104, with the index finger and/or the middle finger supporting directly on the rear surface 57 of the supporting plate 50 to stabilize the angle of the base 40 with respect to the supporting plate 50, and the rest of fingers holding the handle 70.

The needle tip 102A is then inserted into or through the skin 108 until the front surface of the supporting plate 50 fully contacts the skin 108 to support the apparatus 120 of FIG. 7 on the skin 108 as shown in FIG. 8. The user's right hand typically holds and pushes the syringe 106 to advance forward the needle device 107. The screw nut 62 in front of the needle wing 104 blocks further advancement of the needle device 107 by blocking further advancement of the needle wing 104 beyond the location of the screw nut 62. To advance the needle device 107 further, the user drives the screw nut 62 forward further by turning the screw nut 62 forward, and then advances the needle device 107 forward further by pushing the syringe 106 with the right hand. The user repeats driving the screw nut 62 and advancing the needle device 107 several times or more until the tip 102A of the needle 102 enters the targeted tissue or space. The set of ruler marks 44 marked on the top surface 47 of the base 40 helps the user to see how far the needle 102 of the needle device 107 advances with each attempt of the advancement.

To insert the needle 102 with the needle wing 104 into the epidural space 109 for epidural anesthesia, the needle insertion assistance device 1 of FIG. 1 can be used as follows. After the needle 102 is inserted into the interspineous ligament through the skin 108, the syringe 106 is attached to the needle 102 to form the needle device 107. As shown in FIGS. 7 and 9, the needle insertion assistance device 1 of FIG. 1 is then placed under the needle device 107 to form the apparatus 120 of FIG. 7, with the supporting plate 50 placed on the skin 108, the needle wing 104 on the top surface 47 of the base 40, and the syringe 106 on the groove 42, and between the left syringe holding plate 46A and the right syringe holding plate 46B. The screw nut 62 is driven and situated in front of the needle wing 104 as shown in FIGS. 7 and 9.

The base 40 can be rotated on the hinge 54 to form an angle with respect of the supporting plate 50 as the same as an angle at which the needle 102 is inserted into the skin 108. The arm screw 82 is then turned and driven into a tight state to tighten the arm 80 to the arm support 84, so that the arm 80 is unable to slide over the arm screw bolt 85 of the arm screw 82 to allow the angle adjusting assembly 89 to stop the rotation of the base 40 on the hinge 54 to fix the angle of the base 40 with respect to the supporting plate 50 to stabilize the angle at which the needle 102 is inserted into the skin 108. The user's left hand typically holds the apparatus 120 of FIG. 7 with the left thumb over the needle wing 104, the index finger in the space between the front 76 of the handle 70 and the rear surface 57 of the supporting plate 50, and the rest of the fingers of the left hand holding the handle 70 as shown in FIG. 8. The user's right hand typically holds and pushes the syringe 106 to advance the needle device 107. The screw nut 62 in front of the needle wing 104 blocks further advancement of the needle device 107 by blocking further advancement of the needle wing 104 beyond the location of the screw nut 62. To advance the needle device 107 further, the user drives the screw nut 62 forward further by turning the screw nut 62 forward, and then advances the needle device 107 further by pushing the syringe 106 with the right hand. The loss of resistance technique, as a standard technique, is used in each attempt of the advancement to identify if the tip 102A of the needle 102 enters the epidural space 109 as shown in FIG. 8. The user repeats driving the screw nut 62 and advancing the needle device 107 several times or more until the tip 102A of the needle 102 enters the epidural space 109. The needle insertion assistance device 1 of FIG. 1 can be removed and separated from the needle device 107 after the entrance of the tip 102A of the needle 102 into the epidural space 109 is identified with the loss of resistance technique. A catheter is then inserted through the needle 102 into the epidural space 109 followed by removal of the needle 102. A drug can be given through the catheter, which remains in the epidural space 109 during epidural anesthesia.

FIG. 21 is a rear, top, left side perspective view of a needle insertion assistance device 101 in accordance with a second embodiment of the present invention. As shown in FIG. 21, the needle insertion assistance device 101 of FIG. 21 includes a base 140 with a groove 142 and a set of ruler marks 144, a supporting plate 150 with a needle gap 152, and a needle holder 190. The base 140 is connected to the supporting plate 150 by a joint, pivot, or hinge 154. The needle insertion assistance device 101 of FIG. 21 further includes a needle blocker 160, and a handle 170. The needle insertion assistance device 101 of FIG. 21 still further includes an angle adjusting assembly which is not illustrated in FIG. 21. The needle blocker 160 further includes a screw bolt 164 having two ends, a screw nut 162 screwed on the screw bolt 164, a front screw support 166A, and a rear screw support 166B.

The base 140, the supporting plate 150, the needle blocker 160, the handle 170, the hinge 154, and the angle adjusting assembly in the second embodiment of FIG. 21 have the same structures and functions as the corresponding parts, such as the base 40, the supporting plate 50, the needle blocker 60, the handle 70, the hinge 54, and the angle adjusting assembly 89, in the first embodiment of FIG. 1, respectively. The difference between the second embodiment of FIG. 21 and the first embodiment of FIG. 1 is that the second embodiment of FIG. 21 has the needle holder 190, but not any syringe holder, such as the syringe holder 46 in the first embodiment of FIG. 1.

As shown in FIG. 21, the hinge 154 connects the front end of the base 140 to the rear surface of the supporting plate 150. The front screw support 166A and the rear screw support 166B are securely affixed to each end of the screw bolt 164 respectively, and securely affixed to one side of the top surface of the base 140. The top of the handle 170 is securely affixed to the underside of the base 140. In one embodiment of the present invention, the front end of the base 140 is connected to the rear surface of the supporting plate 150 by the hinge 154. However, in alternative embodiments, the front end of the base 140 may be securely affixed to the rear surface of the supporting plate 150 with various degree angles from about ninety to one hundred and sixty degrees between the top surface of the base 140 and the rear surface of the supporting plate 150 above the connection site.

Figure 22:
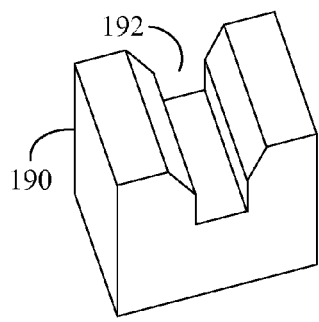
FIG. 22 is a rear, top, left side perspective view of a needle holder for use with the needle insertion assistance device of FIG. 21.
Figure 23:
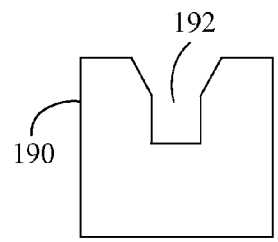
FIG. 23 is a rear plan view of the needle holder of FIG. 22.

The needle holder 190 may be a protrusion, projection or support securely affixed to the frond part of the top surface of the base 140 as shown in FIG. 21. The needle holder 190 has a needle slot 192 which may be a groove or slot longitudinally cut in an upper part of the needle holder 190 as shown in FIGS. 22 and 23. The width of the needle slot 192 may be slightly wider than the diameter of the needle 102 so that the needle slot 192 can slidably hold the needle 102 over the base 140 in a straight line, so that the needle 102, as well as the needle device 107, is able to slide and advance in a straight line, but unable to move from side to side.

Figure 24:
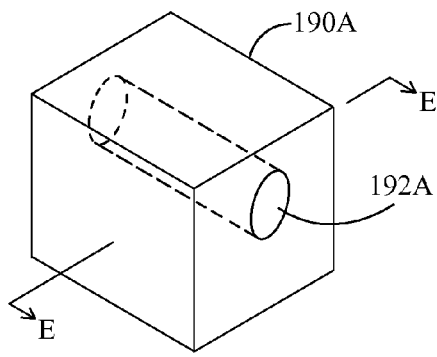
FIG. 24 is a rear, top, left side perspective view of an alternative embodiment of a needle holder for use with the needle insertion assistance device of FIG. 21, excluding the needle holder shown in FIG. 21.
Figure 25:
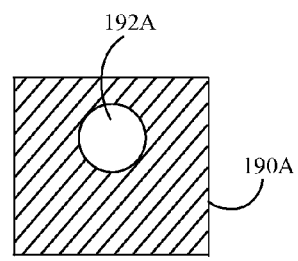
FIG. 25 is a cross-section view of the needle holder of FIG. 24, along a line E-E shown in FIG. 24.

FIGS. 24 and 25 show one alternative embodiment of a needle holder 190A, as an alternative to the needle holder 190, for use with the needle insertion assistance device 101 of FIG. 21, excluding the needle holder 190. The needle holder 190A has a needle hole 192A which may be a opening, tunnel, or hole longitudinally cut through the needle holder 190A as shown in FIGS. 24 and 25. The diameter of the needle hole 192A can be slightly wider than the diameter of the needle 102 so that the needle hole 192A can slidably hold the needle 102 over the base 140 in a straight line, so that the needle 102, as well as the needle device 107, can slide and advance in a straight line.

In one embodiment of the present invention, the longitudinal length of the needle holders 190 and 190A is about one half to five centimeters so that the needle holders 190, or 190A may stably hold the needle 102 over the base 140 in a straight line, and the needle 102, as well as the needle device 107, can advance in a straight line. However, the longitudinal length of the needle holders 190, and 190A may be less than one half centimeter or longer than five centimeters to satisfactorily hold the needle 102 over the base 140 in a straight line, so that the needle 102, as well as the needle device 107, can advance in a straight line.

The operation of the second embodiment of the present invention is described as follows. To insert the needle 102 with the needle wing 104 into a targeted tissue or cavity of a human body, the needle insertion assistance device 101 of FIG. 21 can be used as follows. The syringe 106 is attached to the needle 102 to form the needle device 107. The needle device 107 is then placed into the needle insertion assistance device 101 of FIG. 21 with the needle 102 in the needle slot 192 of the needle holder 190, the needle wing 104 on the top surface of the base 140, and the syringe 106 in the groove 142, and the needle 102 passing through the needle gap 152 of the supporting plate 150. The rest of the operation for the needle insertion assistance device 101 of FIG. 21 may be the same as or similar to the operation for the first embodiment of FIG. 1.

To use an embodiment of FIGS. 24 and 25 with the needle holder 190A with the needle hole 192A, the needle 102 is inserted into the needle hole 192A, and the needle wing 104 on the top surface of the base 140, and then the syringe 106 is attached to the needle 102 and placed in the groove 142. The rest of the operation for the embodiment may be the same as or similar to the operation for the first embodiment of FIG. 1.

To insert the needle 102 with the needle wing 104 into the epidural space 109 for epidural anesthesia, the needle insertion assistance device 101 of FIG. 21 can be used as follows. After the needle 102 is inserted into the interspineous ligament through the skin 108, as shown in FIG. 8, the syringe 106 is attached to the needle 102 to form the needle device 107. The needle insertion assistance device 101 of FIG. 21 is placed under the needle device 107 with the supporting plate 150 on the skin 108 in the same manner as shown in FIG. 8. The needle 102 is placed in the needle slot 192 of the needle holder 190, the needle wing 104 on the top surface of the base 140, the syringe 106 on the groove 142. The rest of the operation for the needle insertion assistance device 101 of FIG. 21 may be the same as or similar to the operation for the first embodiment of FIG. 1 for epidural anesthesia.

Figure 26:
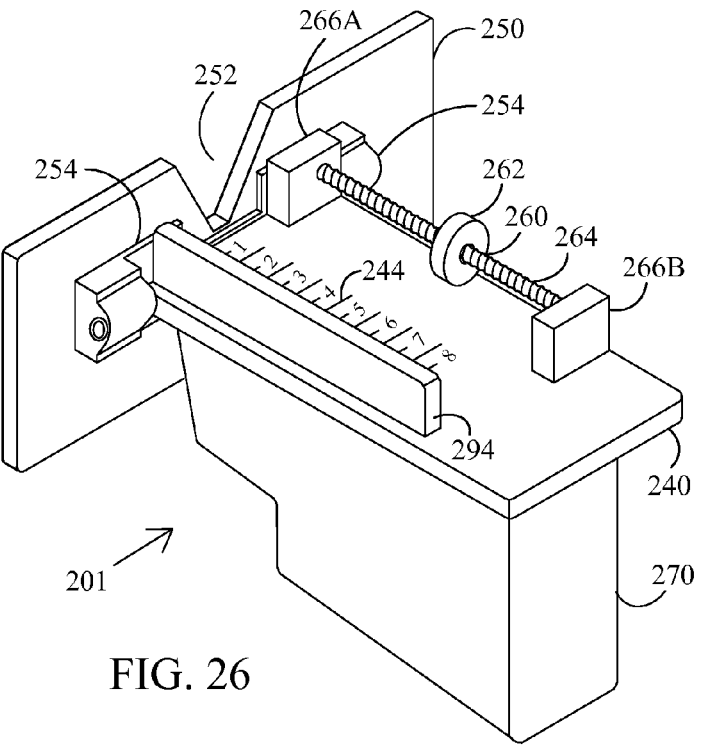
FIG. 26 is a rear, top, left side perspective view of a needle insertion assistance device in accordance with a third embodiment of the present invention.

FIG. 26 is a rear, top, left side perspective view of a needle insertion assistance device 201 in accordance with a third embodiment of the present invention. As shown in FIG. 26, the needle insertion assistance device 201 of FIG. 26 includes a base 240 with a set of ruler marks 244, a supporting plate 250 with a needle gap 252, and a wing holder 294. The base 240 is connected to the supporting plate 250 by a joint, pivot, or hinge 254. The needle insertion assistance device 201 of FIG. 26 further includes a needle blocker 260, and a handle 270. The needle insertion assistance device 201 of FIG. 26 still further includes an angle adjusting assembly which is not illustrated in FIG. 26. The needle blocker 260 further includes a screw bolt 264 having two ends, a screw nut 262 screwed on the screw bolt 264, a front screw support 266A, and a rear screw support 266B.

The supporting plate 250, the needle blocker 260, the handle 270, the hinge 254, and the angle adjusting assembly in the third embodiment of FIG. 26 have the same structures and functions as the corresponding parts, such as the supporting plate 50, the needle blocker 60, the handle 70, the hinge 54, and the angle adjusting assembly 89, in the first embodiment of the FIG. 1, respectively. The base 240 in the third embodiment of FIG. 26 has the same structure as the base 40 in the first embodiment of the FIG. 1, except that the base 240 does not have a groove, such as the groove 42 in the base 40 in the first embodiment of the FIG. 1. Another difference of the third embodiment of FIG. 26 from the first embodiment of FIG. 1 is that the third embodiment of FIG. 26 has the wing holder 294, but not any syringe holder, such as the syringe holder 46 in the first embodiment of FIG. 1.

As shown in FIG. 26, the hinge 254 connects the front end of the base 240 to the rear surface of the supporting plate 250. The front screw support 266A and the rear screw support 266B are securely affixed to each end of the screw bolt 264 respectively, and securely affixed to one side of the top surface of the base 240. The top of the handle 270 is securely affixed to the underside of the base 240. In one embodiment of the present invention, the front end of the base 240 is connected to the rear surface of the supporting plate 250 by the hinge 254. However, in alternative embodiments, the front end of the base 240 may also be securely affixed to the rear surface of the supporting plate 250 with various degree angles from about ninety to one hundred and sixty degrees between the top surface of the base 240 and the rear surface of the supporting plate 250 above the connection site.

Figure 27:
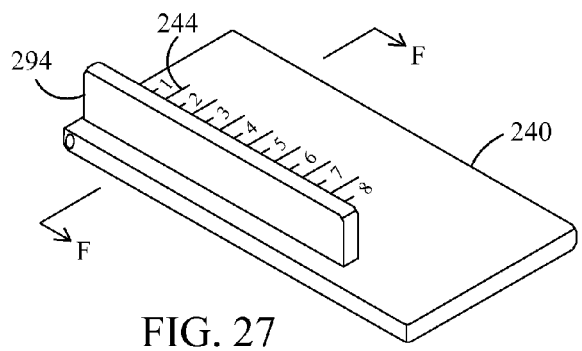
FIG. 27 is a rear, top, left side perspective view of a base and a wing holder for use with the needle insertion assistance device of FIG. 26.
Figure 28:
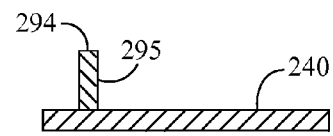
FIG. 28 is a cross-section view of the base and the wing holder of FIG. 27, along a line F-F shown in FIG. 27.

As shown in FIGS. 26, 27, and 28, the wing holder 294 may be a protrusion, projection or plate securely affixed to another side of the top surface of the base 240, opposite to the side where the front screw support 266A and the rear screw support 266B of the needle blocker 260 is securely affixed to. The wing holder 294 has an internal surface 295 as shown in FIG. 28. The wing holder 294 and the screw bolt 264 of the needle blocker 260 together hold both sides of the needle wing 104 of the needle device 107 between the wing holder 294 and the screw bolt 264, so that the needle wing 104, as well as the needle device 107, can advance forward in a straight line, but unable to move from side to side on the base 240. In one embodiment of the present invention, the internal surface 295 of the wing holder 294, which has direct contact with the needle wing 104, is a substantially flat surface as shown in FIGS. 27 and 28. However, in alternative embodiments, the internal surface 295 of the wing holder 294 can be different, such as a curved surface, a angular surface, and/or a combination of a flat surface, a curved surface, a angular surface, etc., to accommodate the configuration of one side of the needle wing 104 so that the needle wing 104, as well as the needle device 107, is able to advance forward in a straight line. As shown in FIG. 28, the internal surface 295 of the wing holder 294 is substantially perpendicular to the top surface of the base 240. However, the internal surface 295 of the wing holder 294 can be inclined to form different angles, such as an obtuse angle, with respect of the top surface of the base 240 in alternative embodiments.

Figure 29:
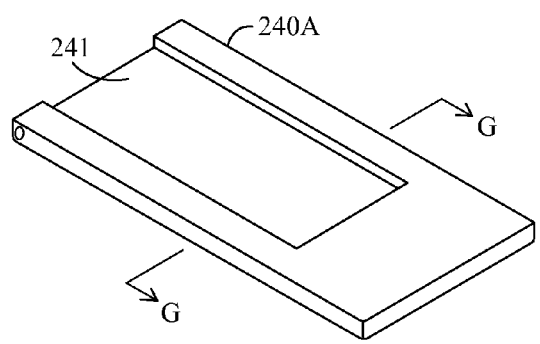
FIG. 29 is a rear, top, left side perspective view of an alternative embodiment of a base with a wing holding groove for use with the needle insertion assistance device of FIG. 26, excluding the base and the wing holder shown in FIG. 26.
Figure 30:
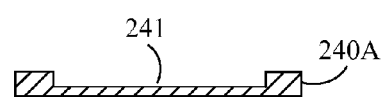
FIG. 30 is a cross-section view of the base with the wing holding groove of FIG. 29, along a line G-G shown in FIG. 29.

FIGS. 29 and 30 show a wing holding groove 241 in accordance with one alternative embodiment of the present invention. The wing holding groove 241 holds the needle wing 104 of the needle 102 for use with the needle insertion assistance device 201 of FIG. 26, excluding the wing holder 294. The wing holding groove 241 may be a groove longitudinally furrowed in the top surface of a base 240A, which replaces base 240 in this embodiment. The width of the wing holding groove 241 is slightly wider than the width of the needle wing 104, so that the wing holding groove 241 can slidably hold the needle wing 104 in a straight line to allow the needle wing 104, as well as the needle device 107, to advance forward in a straight line. In one embodiment of the present invention, the wing holding groove 241 of the FIGS. 29 and 30 has a rectangular cross section, as shown in FIG. 30. However, the wing holding groove 241 may have a different cross section, such as a triangular cross section, a polyangular cross section, and/or a cross section with a curved bottom, etc., to accommodate the configuration of the bottom and two sides of the needle wing 104 so that the needle wing 104, as well as the needle device 107, is able to advance forward in a straight line, but unable to move from side to side inside the wing holding groove 241.

Figure 31:
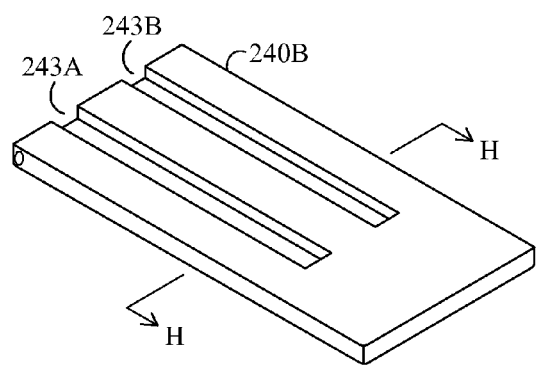
FIG. 31 is a rear, top, left side perspective view of other alternative embodiment of a base with two wing holding grooves for use with the needle insertion assistance device of FIG. 26, excluding the base and the wing holder shown in FIG. 26.
Figure 32:
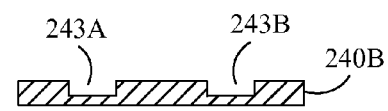
FIG. 32 is a cross-section view of the base with the wing holding grooves of FIG. 31, along a line H-H shown in FIG. 31.

FIGS. 31 and 32 show two wing holding grooves 243A and 243B of another alternative embodiment to hold the needle wing 104 for use with the needle insertion assistance device 201 of FIG. 26, excluding the wing holder 294. The wing holding grooves 243A and 243B may be two grooves longitudinally furrowed in both sides of the top surface of a base 240B, which replaces the base 240 in this embodiment, to hold each side of the needle wing 104 respectively, to allow the needle wing 104, as well as the needle device 107, to be able to advance forward in a straight line, but unable to move from side to side on the base 240B. In one embodiment of the present invention, the wing holding grooves 243A and 243B shown in FIGS. 31 and 32 may each have a rectangular cross section. However, the wing holding grooves 243A and 243B may each have a different cross section, such as a semicircular cross section, a semi-elliptical cross section, a triangular cross section, a polyangular cross section, a cross section with a curved bottom, and/or a combination of a semicircular cross section, a semi-elliptical cross section, a triangular cross section, and a polyangular cross section, etc., to accommodate the configuration of the bottom of the needle wing 104 so that the needle wing 104, as well as the needle device 107, is able to advance forwards in a straight line, but unable to move from side to side on the base 240B.

In one embodiment of the present invention, two wing holding grooves 243A and 243B are furrowed in the top surface of the base 240B. However, in alternative embodiments, only one wing holding groove, or more than two wing holding grooves, may be furrowed in the top surface of the base 240B, like the wing holding grooves 243A and 243B, and can also satisfactorily hold the needle wing 104 of the needle device 107 on the base 240B to allow the needle wing 104, as well as the needle device 107, to advance in a straight line.

Figure 33:
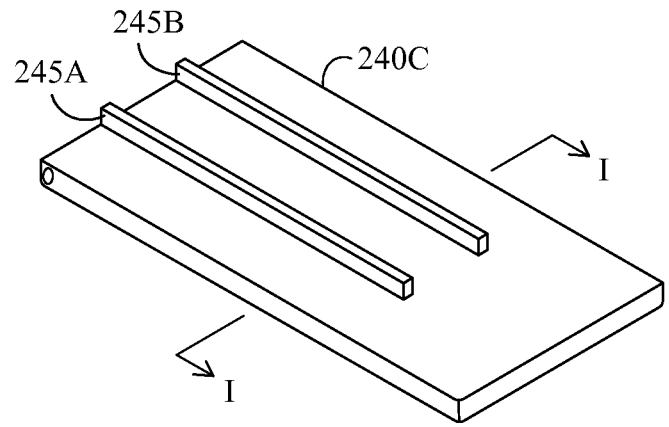
FIG. 33 is a rear, top, left side perspective view of further other alternative embodiment of a base with two wing holding protrusions for use with the needle insertion assistance device of FIG. 26, excluding the base and the wing holder shown in FIG. 26.
Figure 34:
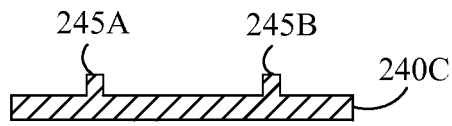
FIG. 34 is a cross-section view of the base with the wing holding protrusions of FIG. 33, along a line I-I shown in FIG. 33.

FIGS. 33 and 34 show two wing holding protrusions 245A and 245B of another alternative embodiment to hold the needle wing 104 for use with the needle insertion assistance device 201 of FIG. 26, excluding the wing holder 294. The wing holding protrusions 245A and 245B may be two projections, or protrusions longitudinally projected from both sides of the top surface of a base 240C, which may replace the base 240 in this embodiment, to hold each side of the needle wing 104 respectively, so that the needle wing 104, as well as the needle device 107, can advance forward in a straight line. In one embodiment of the present invention, the wing holding protrusions 245A and 245B of the FIGS. 33 and 34 may each have a rectangular cross section, as shown in FIG. 34. However, the wing holding protrusions 245A and 245B may each have a different cross section, such as a semicircular cross section, a semi-elliptical cross section, a triangular cross section, a polyangular cross section, a cross section with a curved top, and/or a combination of a semicircular cross section, a semi-elliptical cross section, a triangular cross section, and a polyangular cross section, etc., to accommodate the configuration of the bottom of the needle wing 104, so that the needle wing 104, as well as the needle device 107, is able to advance forward in a straight line, but unable to move from side to side.

In one embodiment of the present invention, two wing holding protrusions 245A and 245B are projected from the top surface of the base 240C. However, in alternative embodiments, only one wing holding protrusion, or more than two wing holding protrusions, projected from the top surface of the base 240C, like the wing holding protrusions 245A and 245B, may also satisfactorily hold the needle wing 104 of the needle device 107 on the base 240C, so that the needle wing 104, as well as the needle device 107, is able to advance forward in a straight line.

Figure 35:
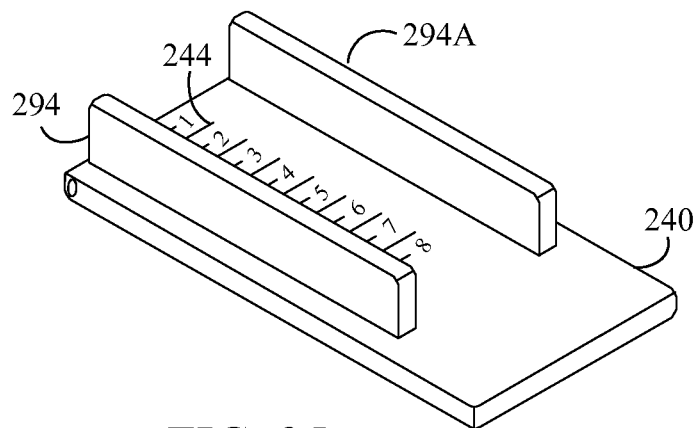
FIG. 35 is a rear, top, left side perspective view of the base and the wing holder of FIG. 27, and another wing holder replacing a needle blocker for use with the needle insertion assistance device of FIG. 26, excluding the needle blocker shown in FIG. 26.

As shown in the FIG. 35, the needle insertion assistance device 201 of FIG. 26 can be further modified by replacing the needle blocker 260 with a wing holder 294A, which has the same structure as the wing holder 294 and is securely affixed to another side of the top surface of the base 240, opposite to the side where the wing holder 294 is securely affixed to. Two wing holders 294 and 294A can together hold the needle wing 104 of the needle device 107 on the base 240 between the wing holders 294 and 294A to allow the needle wing 104, as well as the needle device 107, to be able to advance forward in a straight line, but to be unable to move from side to side. The distance between the wing holders 294 and 294A is slightly wider than the width of the needle wing 104. In this embodiment, a needle blocker, such as the needle blocker 260, is not included.

The wing holder 294 together with the screw bolt 264, the wing holding groove 241, the wing holding grooves 243A and 243B, the wing holding protrusions 245A and 245B, and the wing holder 294A together with the wing holder 294 may be considered to be a wing holding mechanism to hold the needle wing 104 of the needle 102 on a base, such as the base 240, the base 240A, the base 240B, and the base 240C, so that the needle wing 104, as well as the needle device 107, is able to advance forward in a straight line, but unable to move from side to side.

The operation of the third embodiment of FIG. 26 is as follows. To insert the needle 102 with the needle wing 104 into a targeted tissue or cavity of a human body, the needle insertion assistance device 201 of FIG. 26 can be used as follows. The syringe 106 is attached to the needle 102 to form the needle device 107. The needle device 107 is then placed into the needle insertion assistance device 201 of FIG. 26 with the needle wing 104 on the top surface of the base 240, and between the wing holder 294 and the screw bolt 264, the syringe 106 on the top surface of the base 240, and the needle 102 passing through the needle gap 252 of the supporting plate 250. The rest of the operation for the needle insertion assistance device 201 of FIG. 26 may be the same as or similar to the operation for the first embodiment of FIG. 1.

To insert the needle 102 with the needle wing 104 into the epidural space 109 for epidural anesthesia, the needle insertion assistance device 201 of FIG. 26 can be used as follows. After the needle 102 is inserted into the interspineous ligament through the skin 108, the syringe 106 is attached to the needle 102 to form the needle device 107. The needle insertion assistance device 201 of FIG. 26 is placed under the needle device 107 with the supporting plate 250 on the skin 108 in the same manner as shown in FIG. 8. The needle wing 104 is placed on the top surface of the base 240, and between the wing holder 294 and the screw bolt 264. The syringe 106 is placed on the top surface of the base 240. The rest of the operation for the needle insertion assistance device 201 of FIG. 26 may be the same as or similar to the operation for the first embodiment of FIG. 1 for the epidural anesthesia.

The operation of other embodiments with the wing holding groove 241 of FIG. 29, the wing holding grooves 243A and 243B of FIG. 31, and the wing holding protrusions 245A and 245B of FIG. 33 may be the same or similar to that of the embodiment of FIG. 26, except for the replacement of the wing holder 294 with a different wing holding mechanism.

Figure 36:
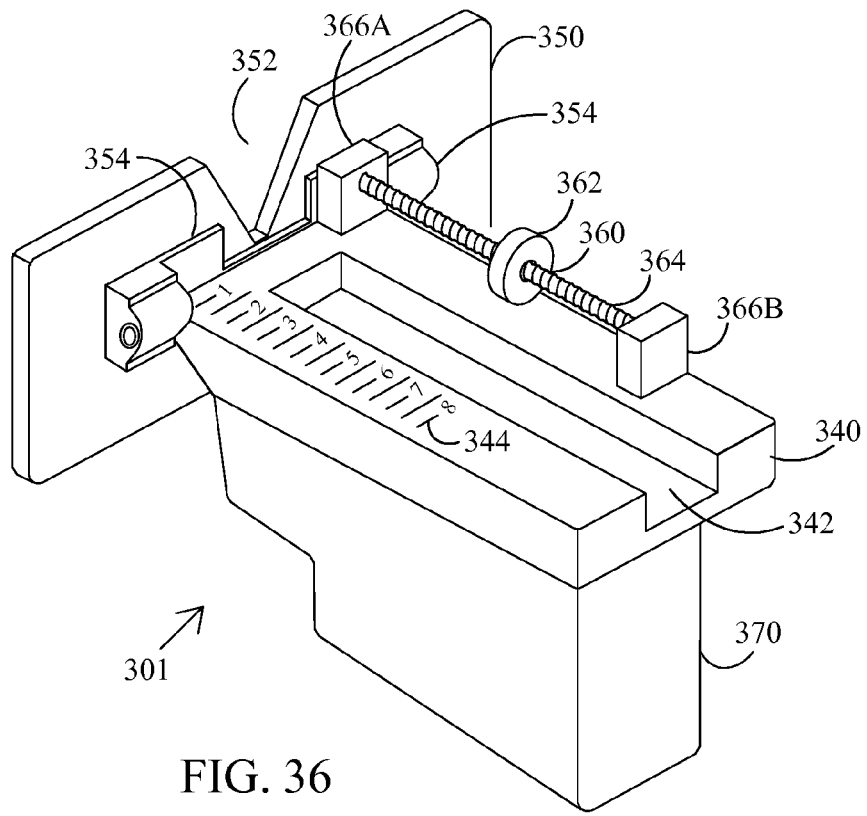
FIG. 36 is a rear, top, left side perspective view of a needle insertion assistance device in accordance with a fourth embodiment of the present invention.

FIG. 36 is a rear, top, left side perspective view of a needle insertion assistance device 301 in accordance with a fourth embodiment of the present invention. As shown in FIG. 36, the needle insertion assistance device 301 of FIG. 36 includes a base 340 with a syringe holding groove 342 and a set of ruler marks 344, and a supporting plate 350 with a needle gap 352. The base 340 is connected to the supporting plate 350 by a joint, pivot, or hinge 354. The needle insertion assistance device 301 of FIG. 36 further includes a needle blocker 360, and a handle 370. The needle insertion assistance device 301 of FIG. 36 still further includes an angle adjusting assembly which is not illustrated in FIG. 36. The needle blocker 360 further includes a screw bolt 364 having two ends, a screw nut 362 screwed on the screw bolt 364, a front screw support 366A, and a rear screw support 366B.

The supporting plate 350, the needle blocker 360, the handle 370, the hinge 354, and the angle adjusting assembly in the fourth embodiment of FIG. 36 have the same structures and functions as the corresponding parts, such as the supporting plate 50, the needle blocker 60, the handle 70, the hinge 54, and the angle adjusting assembly 89, in the first embodiment of FIG. 1, respectively. The difference between the fourth embodiment of FIG. 36 and the first embodiment of FIG. 1 is that the syringe holding groove 342 in the fourth embodiment of FIG. 36 is wider and deeper than the groove 42 in the first embodiment of FIG. 1 in order to receive about one side of the syringe 106, and the fourth embodiment of FIG. 36 dose not include any syringe holder, such as the syringe holder 46 in the first embodiment of FIG. 1.

Figure 37:
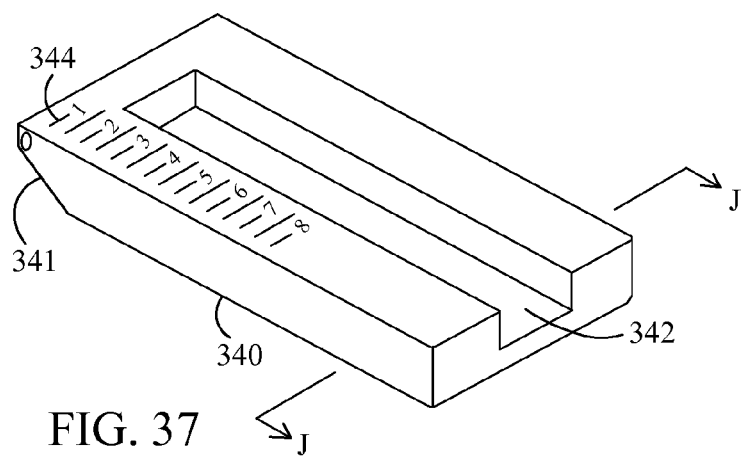
FIG. 37 is a rear, top, left side perspective view of a base with a syringe holding groove for use with the needle insertion assistance device of FIG. 36.

As shown in FIG. 36, the base 340 may be a support, plate, or base to support the screw supports 366A and 366B, and the needle wing 104 of the needle 102, and to allow the groove 342 to be furrowed in. The base 340 has a sloping front end 341 which is made by cutting-off the lower part of the front end of the base 340 as shown in FIG. 37, so that the front end 341 of the base 340 is thinner than the rest part of the base 340 and thin enough to allow the base 340 to be able to rotate on the hinge 354. In one embodiment of the present invention, the base 340 may have a longitudinal length about the same as the length of the syringe 106, a width about three to four times of the diameter of the syringe 106, and a thickness from about one half to one of the diameter of the syringe 106. However, the base 340 may have different sizes, with different longitudinal lengths, widths, and thicknesses in alternative embodiments.

Figure 38:
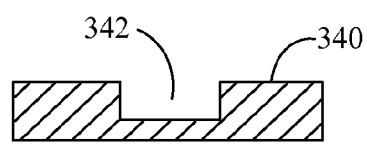
FIG. 38 is a cross-section view of the base with the syringe holding groove of FIG. 37, along a line J-J shown in FIG. 37.

As shown in FIGS. 36-38, the groove 342 may be an indentation, recess, or groove longitudinally furrowed in the top surface of the base 340, and from the edge of the rear end of the base 340 toward the edge of the front end of the base 340. The longitudinal length of the groove 342 may be from about half of the longitudinal length of the base 340 to the longitudinal length of the base 340. The width of the syringe holding groove 342 may be approximately the same as the diameter of the syringe 106. The depth of the syringe holding groove 342 may be about one half of the diameter of the syringe 106. Therefore, the syringe holding groove 342 is sized to receive about one side of the syringe 106 of the needle device 107 to allow the syringe 106, as well as the needle device 107, to be able to advance forward in a straight line, but unable to move from side to side.

In one embodiment of the present invention, as shown in FIGS. 37 and 38, the syringe holding groove 342 may be longitudinally furrowed in about a middle part of the top surface of the base 340. However, the syringe holding groove 342 may be longitudinally furrowed in a different part of the top surface of the base 340, such as in about a left side part, or a right side part of the top surface of the base 340, to function satisfactorily.

In one embodiment of the present invention, the syringe holding groove 342 has a rectangular cross section, as shown in FIG. 38. However, the syringe holding groove 342 may have a different cross section, such as a semicircular cross section, a semi-elliptical cross section, a triangular cross section, a polyangular cross section, a semi-oval cross section, and/or a combination of a semicircular cross section, a semi-elliptical cross section, a triangular cross section, a polyangular cross section, etc., to receive about one side of the syringe 106.

As shown in FIG. 36, the hinge 354 connects the front end 341 of the base 340 to the rear surface of the supporting plate 350. The front screw support 366A and the rear screw support 366B are securely affixed to each end of the screw bolt 364 respectively, and securely affixed to one side of the top surface of the base 340. The top of the handle 370 is securely affixed to the underside of the base 340. In one embodiment of the present invention, the front end 341 of the base 340 is connected to the rear surface of the supporting plate 350 by the hinge 354. However, in alternative embodiments, the front end 341 of the base 340 may be securely affixed to the rear surface of the supporting plate 350 with various degree angles from about ninety to one hundred and sixty degrees between the top surface of the base 340 and the rear surface of the supporting plate 350 above the connection site.

In one embodiment, the set of ruler marks 344 is marked on the top surface of the base 340 with centimeter unit system. However, the set of ruler marks 344 may be marked with a different unit system, such as a millimeter unit system, or an inch unit system, etc.

The operation of the fourth embodiment of FIG. 36 is as follows. To insert the needle 102 with the needle wing 104 into a targeted tissue or cavity of a human body, the needle insertion assistance device 301 of FIG. 36 can be used as follows. The syringe 106 is attached to the needle 102 to form the needle device 107. The needle device 107 is then placed into the needle insertion assistance device 301 of FIG. 36 with the needle wing 104 on the top surface of the base 340, the syringe 106 in the syringe holding groove 342, and the needle 102 passing through the needle gap 352 of the supporting plate 350. The rest of the operation for the needle insertion assistance device 301 of FIG. 36 may be the same as or similar to the operation for the first embodiment of FIG. 1.

To insert the needle 102 with the needle wing 104 into the epidural space 109 for epidural anesthesia, the needle insertion assistance device 301 of FIG. 36 can be used as follows. After the needle 102 is inserted into the interspineous ligament through the skin 108, the syringe 106 is attached to the needle 102 to form the needle device 107. The needle insertion assistance device 301 of FIG. 36 is placed under the needle device 107 with the supporting plate 350 on the skin 108 in the same manner as shown in FIG. 8. The needle wing 104 is placed on the top surface of the base 340. The syringe 106 is placed in the syringe holding groove 342. The rest of the operation for the needle insertion assistance device 301 of FIG. 36 may be the same as or similar to the operation for the first embodiment of FIG. 1 for the epidural anesthesia.

Although the invention has been described by reference to particular illustrative embodiments thereof, many changes and modifications of the invention may become apparent to those skilled in the art without departing from the spirit and scope of the invention. It is therefore intended to include within this patent all such changes and modifications as may reasonably and properly be included within the scope of the present invention's contribution to the art.

I claim:

1. A needle insertion assistance device for use with a needle device, the needle device including a syringe and a needle that has a needle wing and is attached to the syringe, the needle insertion assistance device comprising a base having a front end, a rear end, an underside, and a top surface having two sides and a rear part, to support the needle device on the top surface;

a supporting plate having a front surface for contacting the skin of a patient, and an oppositely facing rear surface to support the needle insertion assistance device and prevent unintentional forward advancement of the needle insertion assistance device;

a handle securely affixed to the underside of the base for a user to hold and use the needle insertion assistance device;

a means for connecting the front end of the base to the rear surface of the supporting plate; and a means for holding the syringe of the needle device on the base;

wherein the means for connecting the front end of the base to the rear surface of the supporting plate connects the front end of the base to the rear surface of the supporting plate along a line wherein a substantial portion of the oppositely facing surface of the supporting plate lies above the line and a substantial portion of the oppositely facing surface of the supporting plate lies below the line, wherein the line is parallel to the front end of the base and perpendicular to a longitudinal axis of the base, and wherein the supporting plate extends longitudinally a first distance above the line and perpendicular to the line in a first direction, and extends longitudinally a second distance below the line and perpendicular to the line in a second direction opposite the first direction, such that the first distance and the second distance are approximately equal;

wherein the means for connecting the front end of the base to the rear surface of the supporting plate connects the front end of the base to the rear surface of the supporting plate so that the base can pivot with respect to the supporting plate;

wherein the top surface of the base is substantially planar, and the rear surface of the supporting plate is substantially planar, and the means for connecting the front end of the base to the rear surface of the supporting plate allows the base to be pivoted with respect to the supporting plate, so that the top surface of the base can be oriented at angles substantially different from ninety degrees with respect to the rear surface of the supporting plate.

2. The needle insertion assistance device of claim 1 wherein the base further includes a groove longitudinally furrowed in the top surface of the base; and whereby the groove is configured to act as a recess to hold a part of one side of the syringe of the needle device on the top surface of the base and is configured to act as a track for the syringe of the needle device to advance in a straight line.

3. The needle insertion assistance device of claim 2 wherein the base has a longitudinal length, and a thickness;

and wherein the groove has a length from about half of the longitudinal length of the base to the longitudinal length of the base, a depth from about half one millimeter to the thickness of the base, and a width smaller than the diameter of the syringe, in order to hold a part of one side of the syringe on the top surface of the base and act as a track for the syringe of the needle device to advance in a straight line.

4. The needle insertion assistance device of claim 1 wherein the means for holding the syringe of the needle device on the base includes at least one syringe holder securely affixed to the rear part of the top surface of the base; and whereby the syringe holder is configured to hold the syringe of the needle device on the base to allow the syringe, as well as the needle device, to be able to advance forward in a straight line, but to be unable to move from side to side.

5. The needle insertion assistance device of claim 4 wherein the syringe holder comprises at least two syringe holding plates securely affixed to the rear part of the top surface of the base, and on both sides of the groove respectively; whereby the syringe holding plates hold the syringe of the needle device on the base and between the syringe holding plates to allow the syringe, as well as the needle device, to be able to advance forward in a straight line, but to be unable to move from side to side.

6. The needle insertion assistance device of claim 1 wherein the means for connecting the front end of the base to the rear surface of the supporting plate includes at least one hinge that allows the base to rotate with respect to the supporting plate to form different angles with respect to the supporting plate.

7. The needle insertion assistance device of claim 1 wherein the handle further includes a sloping bottom, a sloping front, and at least one notch to facilitate handling and hand-held usage of the needle insertion assistance device by a human being.

8. The needle insertion assistance device of claim 1 further comprising a needle blocker including a screw bolt having two ends, a screw nut screwed on the screw bolt, and at least one screw support securely affixed to one end of the screw bolt and securely affixed to one side of the top surface of the base to support the screw bolt and the screw nut over the side of the top surface of the base; and whereby the screw nut prevents the needle device from advancing forward by blocking the needle wing of the needle device from advancing forward beyond a location of the screw nut.

9. The needle insertion assistance device of claim 1 further comprising a means for stopping rotation of the base with respect to the supporting plate to fix an angle of the base with respect to the supporting plate to stabilize an angle at which the needle is inserted into a human body.

10. The needle insertion assistance device of claim 9 wherein the means for stopping rotation of the base with respect to the supporting plate includes an angle adjusting assembly having two ends, and pivotally connected to the rear surface of the supporting plate at one end and slidably connected to the base at another end.

11. The needle insertion assistance device of claim 10 wherein the angle adjusting assembly further includes an arm support securely affixed to the base, an arm screw, and an arm having a sliding gap, and two ends, one end of the arm pivotally connected to the rear surface of the supporting plate and another end of the arm slidably connected to the base by the arm support and the arm screw with the arm screw inserted through the sliding gap of the arm and then screwed into the arm support so that the arm can slide with respect to the arm support and the base over the arm screw;

whereby the arm is able to slide with respect to the arm support and the base over the arm screw when the arm screw is turned and driven into a loose state, and unable to slide with respect to the arm support and the base over the arm screw when the arm screw is turned and driven into a tight state; and whereby the base is unable to rotate with respect to the supporting plate if the arm is unable to slide with respect to the arm support and the base over the arm screw when the arm screw is turned and driven into the tight state.

12. The needle insertion assistance device of claim 1 wherein the supporting plate further includes an upper part, and a first needle gap situated at the upper part of the supporting plate for the needle to pass through the supporting plate; and wherein a left portion of the supporting plate is located to a left of the first needle gap, a right portion of the supporting plate is located to a right of the first needle gap, and a bottom portion of the supporting plate is located below the needle gap;

and wherein the left, the right, and the bottom portions of the supporting plate together form a triangular shape.

13. The needle insertion assistance device of claim 1 wherein the base further includes at least one set of ruler marks marked on the top surface of the base to indicate how far the needle advances with each attempt of advancement.

* * * * *